(12) United States Patent
Reynolds et al.

(10) Patent No.: US 7,893,072 B2
(45) Date of Patent: Feb. 22, 2011

(54) TRP-P8 ACTIVE COMPOUNDS AND THERAPEUTIC TREATMENT METHODS

(75) Inventors: Mark Reynolds, Millbrae, CA (US); Paul Polakis, Burlingame, CA (US)

(73) Assignee: Genentech, Inc., South San Francisco, CA (US)

(*) Notice: Subject to any disclaimer, the term of this patent is extended or adjusted under 35 U.S.C. 154(b) by 1234 days.

(21) Appl. No.: 10/884,379

(22) Filed: Jul. 2, 2004

(65) Prior Publication Data
US 2005/0090514 A1    Apr. 28, 2005

Related U.S. Application Data

(60) Provisional application No. 60/484,526, filed on Jul. 2, 2003, provisional application No. 60/491,616, filed on Jul. 31, 2003.

(51) Int. Cl.
*A01N 43/54* (2006.01)
*A01N 43/42* (2006.01)
*A61K 31/58* (2006.01)

(52) U.S. Cl. .................. 514/269; 514/284; 514/176
(58) Field of Classification Search .................. 514/269
See application file for complete search history.

(56) References Cited

U.S. PATENT DOCUMENTS

| | | | |
|---|---|---|---|
| 3,821,221 A | 6/1974 | Podesva et al. | |
| 4,060,091 A | 11/1977 | Watson et al. | |
| 4,070,496 A | 1/1978 | Rowsell et al. | |
| 4,136,163 A | 1/1979 | Watson et al. | |
| 4,150,052 A | 4/1979 | Watson et al. | |
| 4,178,459 A | 12/1979 | Watson et al. | |
| 4,190,643 A | 2/1980 | Watson et al. | |
| 4,193,936 A | 3/1980 | Watson et al. | |
| 4,226,988 A | 10/1980 | Watson et al. | |
| 6,497,859 B1 | 12/2002 | Zanone et al. | 424/49 |
| 6,582,959 B2 | 6/2003 | Kim | |
| 7,045,624 B2 | 5/2006 | Foster et al. | |
| 2003/0108963 A1 | 6/2003 | Schlegel et al. | |
| 2004/0161751 A1 | 8/2004 | Wei | |
| 2005/0054651 A1 | 3/2005 | Natarajan et al. | 514/249 |
| 2007/0010574 A1 | 1/2007 | Plath et al. | |

FOREIGN PATENT DOCUMENTS

| | | |
|---|---|---|
| FR | 2 127 013 A1 | 10/1972 |
| GB | 1351761 | 5/1974 |
| GB | 1361192 | 7/1974 |
| GB | 1457671 | 12/1976 |
| WO | WO 94/05291 | 3/1994 |
| WO | WO 95/11699 | 5/1995 |
| WO | WO 00/33856 | 6/2000 |
| WO | 02/15692 | 2/2002 |
| WO | WO 02/16429 A3 | 2/2002 |
| WO | WO 02/16602 A3 | 2/2002 |
| WO | WO 03/092697 A1 | 11/2003 |
| WO | WO 2004/026840 A1 | 4/2004 |
| WO | WO 2004/054497 A2 | 7/2004 |

OTHER PUBLICATIONS

Brawley et al., The Future of Prostate Cancer Prevention, Annals of the New York Academy of Sciences 952: 145-152 (2001).*
Fleig, A. et al., "The TRPM ion channel subfamily: molecular, biophysical and functional features," *TRENDS in Pharmacological Sciences*, vol. 25, No. 12, pp. 633-639 (Dec. 2004).
Montell, C., "Thermosensation: Hot Findings Make Dispatch TRPNs Very Cool," *Current Biology*, vol. 13, No. 12, pp. R476-R478 (Jun. 17, 2003).
Yamamura et al, Am J Physiol Cell Physiol 295: C296-301, 2008.
European Search Report dated Sep. 6, 2007.
Clapham, D. et al., "The TRP Ion Channel Family," *Nature Reviews, Neuroscience*, vol. 2, pp. 387-396 (Jun. 2001).
Cunningham, D. et. al., *J. Chem. Soc., Perkin Trans.* I, 2002, 2692-2698.
Fuessel, et al International Journal of Oncology (2003), 23(1):221-228.
Henshall, et al Cancer Research (2003), 63(14):4196-4203.
Kiessling, et al (2003) Prostate 56(4):270-279.
McKemy, D. et al., "Identification of a Cold Receptor Reveals a General Role for TRP Channels in Thermosensation," *Nature*, vol. 416, No. 6876, pp. 52-58 (Mar. 7, 2002).
Nealen et al Journal of neurophysiology (Jul. 2003), 90(1):515-20.
Okazawa et al Neuroscience letters (Apr. 8, 2004), 359(1-2):33-6.
Ottinger, H. et al., Systematic Studies on Structures and Physiological Activity of Cyclic α-Keto Enamines, a Novel Class of "Cooling Compounds," *J. Agric. Food Chem.*, vol. 49, pp. 5383-5390 (2001).
Skryma, R. et al., "store depletion and store-operated $Ca^{2+}$ current in human prostate cancer LNCaP cells: involvement in apoptosis," *J. Physiology*, vol. 527, No. 1, pp. 71-83 (2000).
Thut et al., Neuroscience (2003), 119(4):1071-83.
Tsavaler, et al Cancer Research (2001), 61(9):3760-3769.
Watson, H. et al., "New Compounds with the Menthol Cooling Effect," *J. Soc. Cosmet. Chem.*, vol. 29, pp. 185-200 (1978).
Wei, E. et al., "Communications, AG-3-5: a chemical producing sensations of cold," *J. Pharm. Pharmacol.*, vol. 35, No. 2, pp. 110-112 (1983).

\* cited by examiner

*Primary Examiner*—Sreeni Padmanabhan
*Assistant Examiner*—Timothy E Betton
(74) *Attorney, Agent, or Firm*—Merchant & Gould P.C.

(57) ABSTRACT

Compounds of the disclosure provide compositions, which are effective for prophylaxis and treatment of diseases or disorders, such as cell-proliferation, angiogenesis, or apoptosis mediated diseases. The disclosure encompasses compounds, analogs, prodrugs, metabolites, and pharmaceutically acceptable salts thereof, pharmaceutical compositions, and methods for prophylaxis and treatment of diseases and other maladies or conditions involving cancer, tumors, and like conditions. The disclosure also provides therapeutic methods including the administration of an effective amount of a compound of the disclosure.

13 Claims, 5 Drawing Sheets

TRP-P8 ACTIVE COMPOUNDS AND THERAPEUTIC TREATMENT METHODS

RELATED APPLICATIONS

This application is a United States non-provisional application and is related to and claims priority to co-pending U.S. provisional application Ser. Nos. 60/484,526, filed Jul. 2, 2003, and 60/491,616, filed Jul. 31, 2003, the disclosures of which are incorporated herein by reference in their entirety.

BACKGROUND

Compounds which produce a physiological cool sensation when applied to the skin are known, see for example, "New Compounds with the Menthol Cooling Effect," H. R. Watson, et al., *J. Soc. Cosmet. Chem.*, 1978, 29, 185-200.

Wei, E. T., et al., *J. Pharm. Pharmacol.*, 1983, 35(2), 110-112, describe a compound named "icilin" for its cool-sensation producing properties, (also known as AG-3-5) or 3-(2-Hydroxy-phenyl)-6-(3-nitro-phenyl)-3,4-dihydro-1H-pyrimidin-2-one, of the formula:

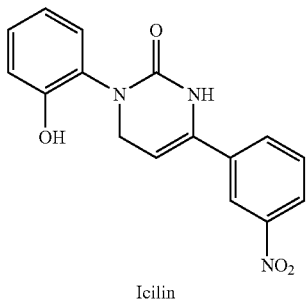

Icilin

Still other compounds having cooling action have been recently reported, see H. Ottinger, et al., *J. Agric. Food Chem.*, 2001, 49, 5383-5390.

U.S. Pat. No. 4,150,052, discloses menthane carboxamide compounds, for example, of the formula IIa3-1:

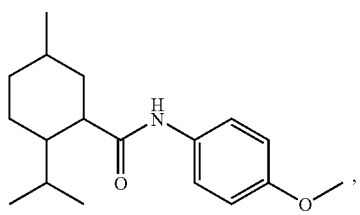

IIa3-1 that are reported to have a physiological cooling action on the skin.

U.S. Pat. No. 4,070,496, discloses certain phosphine oxide ($R_1R_2R_3P=O$) compounds and compositions that are reported to have a physiological cooling action on the skin.

U.S. Pat. No. 3,821,221, discloses certain tetrahydropyrimidine-2-one compounds that are reported to have central nervous system activity as depressants or stimulants.

Recently, certain TRP receptors have been shown to have a role in thermosensation, see D. D. McKemy, et al., "Identification of a Cold Receptor Reveals a General Role for TRP Channels in Thermosensation," *Nature*, Mar. 7, 2002; 416 (6876):52-8. For a recent review of "The TRP Ion Channel Family," see D. E. Clapham, et al., *Nature Reviews, Neuroscience*, 2001, 2, 387-396 <www.nature.com/reviews/neuro>. Okazawa et al Neuroscience letters (Apr. 8, 2004), 359(1-2):33-6; Nealen et al Journal of neurophysiology (2003 July), 90(1):515-20; Thut et al., Neuroscience (2003), 119(4): 1071-83.

The gene Trp-p8 was discovered by screening a prostate-specific subtracted cDNA library. The predicted protein has significant homology with the transient receptor potential (Trp) family of $Ca^{2+}$ channel proteins. Northern blot analysis indicates Trp-p8 expression within normal human tissues is mostly restricted to prostate epithelial cells. In situ hybridization analysis shows that Trp-p8 mRNA expression was at moderate levels in normal prostate tissue and appears to be elevated in prostate cancer. Trp-p8 mRNA was also expressed in a number of non-prostatic primary tumors of breast, colon, lung, and skin origin, whereas transcripts encoding Trp-p8 were hardly detected or not detected in the corresponding normal human tissues (Tsavaler, et al Cancer Research (2001), 61(9):3760-3769).

Immunotherapy of prostate carcinoma (PCa) largely depends on the identification of suitable target antigens that are present in a high percentage of prostate tumors. The putative calcium channel protein, Trp-p8, is associated with loss of Trp-p8 mRNA expression and a significantly shorter time to PSA relapse-free survival. The identification of Trp-p8 is associated with prostate cancer outcome, and suggests an integral role for this receptor in prostate carcinogensis. Immunogenic peptides derived from the prostate-specific protein transient receptor potential-p8 (Trp-p8) that is recognized by cytotoxic T lymphocytes from PCa patients have been reported (Kiessling, et al (2003) Prostate 56(4):270-279; Henshall, et al Cancer Research (2003), 63(14):4196-4203; Fuessel, et al International Journal of Oncology (2003), 23(1):221-228; U.S. Pat. No.2003-108,963 A1). Identification of therapeutic agents effective in the treatment of neoplastic, hyperplastic, and like diseases or conditions continues to be the subject of significant research efforts. Recent work indicates that certain therapeutic agents in combination with certain antibody preparations can be effective in treating angiogenic related disorders, and like diseases or conditions, see for example, U.S. Pat. No. 6,582,959.

There is currently a need for therapeutic agents and methods that are useful to treat diseases and conditions that are associated with regulation of the Trp-p8 receptor. There is also a need for therapeutic agents and treatment methods, which are specific and selective toward cancerous cells and have low cytotoxicity toward healthy cells. There is also a need for therapeutic agents in combination with additional chemotherapeutic agents, including, for example, antibody preparations, and combination therapeutic treatment methods thereof, that are useful to treat diseases and conditions that are associated with regulation of the Trp-p8 receptor.

SUMMARY

It has now been discovered certain compounds, including some known to produce a physiological cool sensation ("cool-genic"), such as the above mentioned tetrahydropyrimidine-2-ones, phosphine oxides, menthane carboxamide compounds, alkyl substituted alkyl amide compounds, and alpha-keto enamines, exhibit useful biological activity, such as anti-tumor activity.

Accordingly, the present disclosure provides, in exemplary embodiments, compounds which activate the Trp-p8 receptor. In embodiments, the present disclosure provides compounds and treatment methods, which cause increased calcium ion flow into cancerous cells (i.e., "flux activating" or "flux promoting" compounds). In embodiments, the present disclosure provides compounds, pharmaceutical compositions, and treatment methods, which inhibit or kill cancerous cells, for example, by causing apoptosis.

In embodiments, the present disclosure also provides:

a pharmaceutical composition comprising a compound of the disclosure and a pharmaceutically acceptable excipient (the composition preferably comprises a therapeutically effective amount of the compound or salt);

a pharmaceutical composition for use in the treatment of tumors, which comprises a compound of the disclosure, and combinations thereof, or a pharmaceutically acceptable salt thereof, and a pharmaceutically acceptable carrier.

a method for treating a disease or condition in a mammal (e.g., a human) wherein a Trp-p8 receptor is implicated and modulation of receptor function is desired comprising administering an effective modulatory amount of a compound of the disclosure;

a method for treating or preventing a disease or Trp-p8 receptor related condition (e.g., tumors) in a mammal comprising administering a therapeutically effective amount of a compound of the disclosure;

a compound of the disclosure for use in medical diagnosis or therapy (e.g., the treatment or prevention of Trp-p8 receptor related disease or condition such as tumors);

the use of a compound of the disclosure to prepare a medicament useful for treating or preventing a disease or Trp-p8 receptor related condition (e.g., the treatment or prevention of Trp-p8 receptor related disease or condition such as tumors);

a method of treating cancer, for example, tumors, comprising administering to a mammal in need of such treatment, an effective amount of a compound of the disclosure;

a method for modulating Trp-p8 receptor function comprising administering an effective modulatory amount of a compound of the disclosure; and a method for modulating Trp-p8 receptor function comprising contacting an Trp-p8 receptor with an effective modulatory amount of a compound of the disclosure.

We have also discovered certain compounds of the disclosure, for example, those compounds known to produce a physiological cool sensation ("cool-genic") and structurally related compounds, such as the above mentioned tetrahydropyrimidine-2-ones, phosphine oxides, menthane carboxamide compounds, alkyl substituted alkyl amide compounds, alpha-keto enamines, and like compounds, when used in combination with additional chemotherapeutic agents, including, for example, antibodies, are capable of useful biological activity, such as anti-tumor activity.

Accordingly, the present disclosure provides in embodiments, therapeutic combinations of a compound of the disclosure (which can activate the Trp-p8 receptor), and additional chemotherapeutic agents, including, for example, an antibody. In embodiments, the present disclosure provides such therapeutic combinations which can be effective in the treatment of cancerous cells. In embodiments, the present disclosure provides such therapeutic combinations and treatment methods thereof, which can be effective in inhibiting or killing cancerous cells, for example, by causing apoptosis, inhibiting angiogenesis, or both.

In embodiments, the present disclosure also provides:

a composition comprising a compound of the disclosure in combination with an antibody and a pharmaceutically acceptable carrier;

a pharmaceutical composition comprising therapeutic combinations of a compound of the disclosure and an antibody, and a pharmaceutically acceptable excipient (the composition preferably comprises a therapeutically effective amount of the compound or salt and a therapeutically effective amount of at least one additional chemotherapeutic agent, for example, an anti-angiogenic antibody);

a pharmaceutical composition for use in the treatment of tumors, which comprises an effective amount of a compound of the disclosure, or a pharmaceutically acceptable salt thereof, in combination with an effective anti-tumor amount of at least one additional chemotherapeutic agent, for example, an anti-angiogenic antibody, and a pharmaceutically acceptable carrier;

a method for treating a disease or condition in a mammal (e.g., a human) wherein a Trp-p8 receptor is implicated (e.g., wherein the disease or condition is characterized by overexpression Trp-p8 receptors) and modulation of receptor function is desired comprising administering an effective modulatory amount of a compound of the disclosure in combination with an effective anti-cancer amount of at least one additional chemotherapeutic agent, for example, an anti-angiogenic antibody;

a method for treating or preventing a disease or Trp-p8 receptor related condition (e.g., tumors) in a mammal comprising administering a therapeutically effective amount of a combination of compound of the disclosure and at least one additional chemotherapeutic agent, for example, an anti-angiogenic antibody;

a compound of the disclosure in combination with at least one additional chemotherapeutic agent, for example, an effective amount of an anti-angiogenic antibody for use in medical diagnosis or therapy (e.g., the treatment or prevention of Trp-p8 receptor related disease or condition such as tumors);

the use of a compound of the disclosure in combination with an effective amount of at least one additional chemotherapeutic agent, for example, an anti-angiogenic antibody to prepare a medicament useful for treating or preventing a disease or Trp-p8 receptor related condition (e.g., the treatment or prevention of Trp-p8 receptor related disease or condition such as tumors);

a method of treating cancer, for example, tumors, comprising administering to a mammal in need of such treatment, an effective amount of a compound of the disclosure in combination with an effective amount of at least one additional chemotherapeutic agent, for example, an anti-angiogenic antibody;

a method for modulating Trp-p8 receptor function comprising administering an effective modulatory amount of a compound of the disclosure in combination with an effective amount of at least one additional chemotherapeutic agent, for example, an anti-angiogenic antibody; and a method for modulating Trp-p8 receptor function comprising contacting an Trp-p8 receptor with an effective modulatory amount of a compound of the disclosure in combination with an effective amount of at least one additional chemotherapeutic agent, for example, an anti-angiogenic antibody.

We have also discovered certain other compounds, such as certain menthane carboxamide compounds described below, characterized in that they also exhibit useful biological activity, such as cell killing anti-tumor activity.

Accordingly, in embodiments, the present disclosure also provides compounds of the formula IIa:

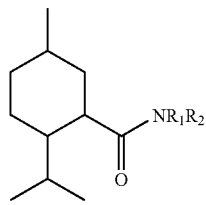

IIa wherein $R_1$ is H, or ($C_1$-$C_6$)alkyl;

$R_2$ is phenyl or a substituted phenyl of the formula (—Ph$R_3R_4R_5R_6R_7$)

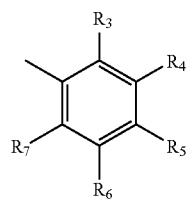

where $R_3$, $R_4$, $R_6$, and $R_7$ are each independently —H, ($C_1$-$C_6$)alkyl, ($C_1$-$C_6$)alkoxyl, or halo;

$R_5$ is halo, ($C_1$-$C_6$)alkyl, ($C_3$-$C_{12}$)cycloalkyl, ($C_1$-$C_6$)alkoxyl, —C(=O)($C_1$-$C_6$)alkyl or ($C_1$-$C_7$)alkanoyl;

or $R_5$ is —N$R_8R_9$, where $R_8$ and $R_9$ are each independently —H, ($C_1$-$C_6$)alkyl, or $R_8$ and $R_9$ together with the nitrogen to which they are attached form a morpholino, pyrrolidino, piperidino, piperzino, indolino, benzimidazolino, azetidino, aziridino, azepino, 1,4-oxazino, or thiomorpholino ring;

or $R_4$ and $R_5$ together with the phenyl to which they are attached form a ring having 4 to 7 atoms and the ring having from 1 to 3 unsaturations; and stereoisomeric forms, mixtures of stereoisomeric forms; or a pharmaceutically acceptable salt thereof, provided that when $R_3$, $R_4$, $R_6$, and $R_7$ of —Ph$R_3R_4R_5R_6R_7$ are —H, $R_5$ is other than —CH$_3$, —OCH$_3$, —OH, —F, or —NO$_2$; and provided that $R_2$ is other than 3-hydroxy-4-methyl-phenyl; and further provided that $R_2$ is other than 2-hydroxy-naphthyl, or pyridyl.

In embodiments, the present disclosure also provides a compound of the above mentioned formula IIa, which is characterized in that the compound is effective in killing cells expressing TRP-p8 but where the calcium ion flux of the expressing cell need not be substantially changed by the presence of the compound.

In embodiments, the present disclosure also provides:

a method for killing target cells which express Trp-p8 but without substantially changing the calcium flux characteristics of the target cells (e.g., tumors) in a mammal comprising administering a therapeutically effective amount of a compound of the disclosure of the formula IIa;

a method for treating a disease or condition in a mammal (e.g., a human) comprising administering an effective amount of a compound of the disclosure of the formula IIa, which compound is cytotoxic with respect to the Trp-p8 receptor and increased calcium ion flux;

a method for treating or preventing a disease or Trp-p8 receptor related condition (e.g., tumors) in a mammal comprising administering a therapeutically effective amount of a compound of the disclosure of the formula IIa, which compound is cytotoxic with respect to the Trp-p8 receptor; and any of the above methods for killing cells, for treating a disease or condition, or treating or preventing a disease comprising administering a therapeutically effective amount of a compound of the disclosure of the formula IIa in combination with another compound of the disclosure, an anti-angiogenic antibody, or mixtures thereof.

These and other embodiments are illustrated herein.

DETAILED DESCRIPTION

Figure 1A:
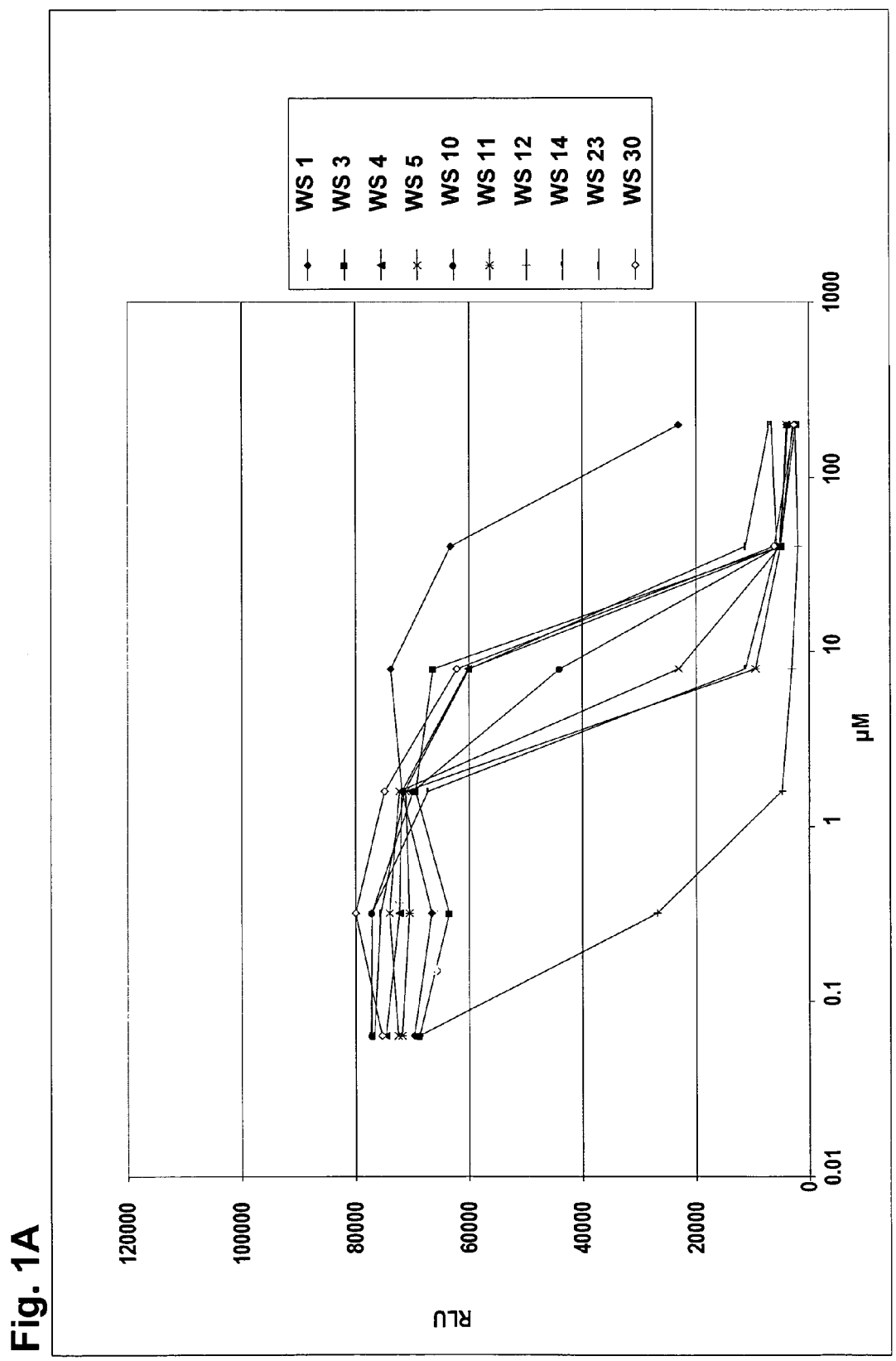
FIGS. 1A-D illustrate the effectiveness of selected coolgenic compounds of the present disclosure in killing human cells expressing Trp-p8 compared to the relative insensitivity of human cells not expressing Trp-p8.

The present disclosure provides the abovementioned pharmaceutical compositions and methods of treatment. The present disclosure also provides the abovementioned compounds of the disclosure of the formula IIa, pharmaceutical compositions including a compound of the disclosure of the formula IIa, and methods of treatment therewith, and which compounds, and pharmaceutical compositions, are cytotoxic to Trp-p8 expressing cells.

Examples of cool-genic compounds are, for example, a compound of the formulas (I-XIII):

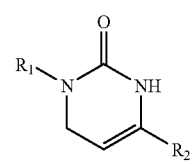

I wherein $R_1$ and $R_2$ are each independently H, alkyl, Het, or aryl, or as disclosed in U.S. Pat. No. 3,821,221;

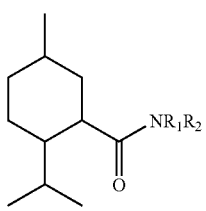

II wherein $R_1$ and $R_2$ are each independently H, alkyl, or aryl, or as disclosed, for example, in U.S. Pat. No. 4,150,052, and *J. Soc. Cosmet. Chem.*, 1978, 29, 185-200;

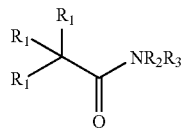

III wherein $R_1$, $R_2$, and $R_3$ are each independently H, alkyl, or aryl, or as disclosed, for example, in *J. Soc. Cosmet. Chem.*, 1978, 29, 185-200 (and references cited therein such as reference 1);

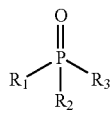

IV wherein $R_1$, $R_2$, and $R_3$ are each independently linear or branched alkyl or cycloalkyl, or as disclosed, for example, in U.S. Pat. No. 4,070,496;

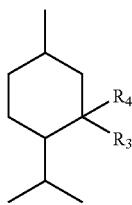

V wherein $R_3$ is —OH, —S(O)$R_1$, —P(=O)$R_1R_2$, —CO$_2$H, —C(=O)NH$_2$, —OC(=O)—CH(OH)—CH$_3$, —C(=O) OC$_n$H$_{2n}$—OH, where n is 1-4, —NR$_1$—C(=O)NR$_1$R$_2$, —SO$_2$R$_1$, —SO$_2$NR$_1$R$_2$, —SONR$_1$R$_2$, and where R$_1$ and R$_2$ are each independently H, alkyl, or aryl, and R$_4$ is H, or R$_3$ and R$_4$ taken together with the carbon atom to which they are attached is a 5-member ketal ring optionally having an hydroxymethyl substituent of the formula —OCH$_2$—CH (CH$_2$—OH)—O—, or as disclosed, for example, in *J. Soc. Cosmet. Chem.*, 1978, 29, 185-200;

a core selected from the (—X) substituted cyclic or branched hydrocarbons of group VI:

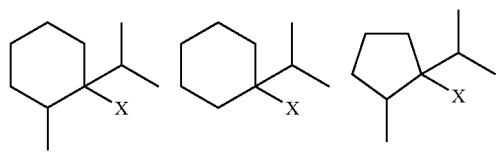

VI

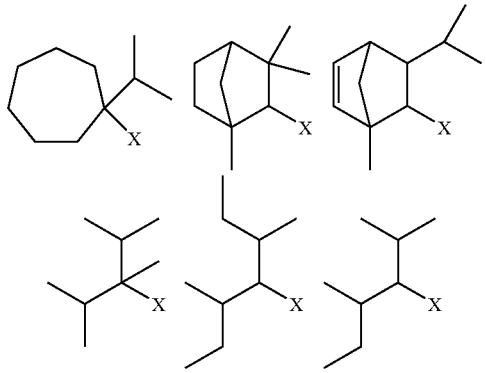

-continued wherein X is an N-alkyl carboxamide, —C(=O)NR$_1$R$_2$, where R$_1$ and R$_2$ are each independently H, alkyl, or aryl, or R$_1$ and R$_2$ taken together with the nitrogen atom to which they are attached is a 5- or 6-membered saturated or unsaturated heterocyclic (Het) ring which is optionally substituted with an oxygen (—O—) ring heteroatom, or as disclosed, for example, in *J. Soc. Cosmet. Chem.*, 1978, 29, 185-200;

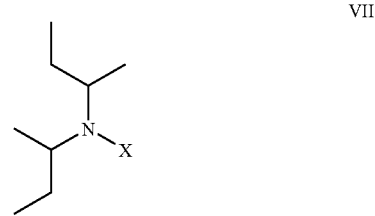

VII wherein X is an N-alkyl carboxamide, —C(=O)NHR$_1$, where R$_1$ is alkyl or substituted alkyl, such as in —C(=O) NHEt or —C(=O)NHCH$_2$CO$_2$Et, or alkyl sulfone, such as in —SO$_2$Et, or as disclosed, for example, in *J. Soc. Cosmet. Chem.*, 1978, 29, 185-200;

alkyl substituted urea compounds, for example, of the formula VIII:

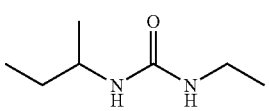

VIII or as disclosed, for example, in *J. Soc. Cosmet. Chem.*, 1978, 29, 185-200;

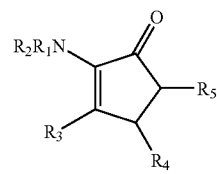

IX wherein R₁ and R₂ are each independently alkyl, or

R₁ and R₂ taken together with the nitrogen atom to which they are attached is a 5- or 6-membered saturated or unsaturated heterocyclic (Het) ring which is optionally substituted with an oxygen (—O—) ring heteroatom, such as a morpholino-ring, and the ring can be optionally substituted with an alpha-CO₂H or an alpha-CO₂CH₃ substituent, and R₃, R₄, and R₅ are each independently H or alkyl, or as disclosed, for example, in *J. Agric. Food Chem.*, 2001, 49, 5383-5390;

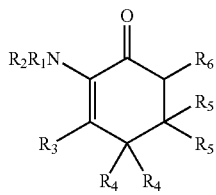

X wherein R₁ and R₂ are each independently alkyl, or R₁ and R₂ taken together with the nitrogen atom to which they are attached is a 5- or 6-membered saturated or unsaturated heterocyclic (Het) ring, and R₃, R₄, R₅, and R₆ are each independently H or alkyl, or as disclosed, for example, in *J. Agric. Food Chem.*, 2001, 49, 5383-5390;

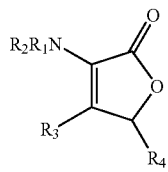

XI wherein R₁ and R₂ are each independently alkyl, or

R₁ and R₂ taken together with the nitrogen atom to which they are attached is a 5- or 6-membered saturated or unsaturated heterocyclic (Het) ring, and R₃ and R₄ are each independently H or alkyl, or as disclosed, for example, in *J. Agric. Food Chem.*, 2001, 49, 5383-5390;

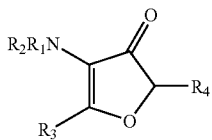

XII wherein R₁ and R₂ are each independently alkyl, or

R₁ and R₂ taken together form a 5- or 6-membered saturated or unsaturated ring, and R₃ and R₄ are each independently H or alkyl, or as disclosed, for example, in *J. Agric. Food Chem.*, 2001, 49, 5383-5390; or

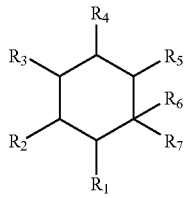

XIII wherein R₁ to R₅ are each independently H, alkyl, or aryl, R₆ is —OH, —S(O)R₈, —P(=O)R₈R₉, —CO₂H, —C(=O)NH₂, —OC(=O)—CH(OH)—CH₃, —C(=O)OC$_n$H$_{2n}$—OH, where n is 1-4, —NR₈—C(=O)NR₈R₉, —SO₂R₈, —SO₂NR₈R₉, or —SONR₈R₉, and where the R₈ and R₉ of R₆ are each independently H, alkyl, or aryl, and R₇ is H, or R₆ and R₇ taken together with the carbon atom to which they are attached is a 5-member ketal ring, having an hydroxymethyl substituent, of the formula —OCH₂—CH(CH₂—OH)—O—;

or a pharmaceutically acceptable salt thereof.

The following definitions are used, unless otherwise described: halo is fluoro, chloro, bromo, or iodo. Alkyl, alkoxy, etc., denote both straight and branched groups; but reference to an individual radical such as "propyl" embraces only the straight chain radical, a branched chain isomer such as "isopropyl" being specifically referred to.

"Alkyl" is C₁-C₁₈ hydrocarbon containing normal, secondary, tertiary or cyclic carbon atoms. Examples are methyl (Me, —CH₃), ethyl(Et, —CH₂CH₃), 1-propyl(n-Pr, n-propyl, —CH₂CH₂CH₃), 2-propyl(i-Pr, i-propyl, —CH(CH₃)₂), 1-butyl(n-Bu, n-butyl, —CH₂CH₂CH₂CH₃), 2-methyl-1-propyl(i-Bu, i-butyl, —CH₂CH(CH₃)₂), 2-butyl(s-Bu, s-butyl, —CH(CH₃)CH₂CH₃), 2-methyl-2-propyl(t-Bu, t-butyl, —C(CH₃)₃), 1-pentyl(n-pentyl, —CH₂CH₂CH₂CH₂CH₃), 2-pentyl (—CH(CH₃)CH₂CH₂CH₃), 3-pentyl(—CH(CH₂CH₃)₂), 2-methyl-2-butyl(—C(CH₃)₂CH₂CH₃), 3-methyl-2-butyl(—CH(CH₃)CH(CH₃)₂), 3-methyl-1-butyl(—CH₂CH₂CH(CH₃)₂), 2-methyl-1-butyl(—CH₂CH(CH₃)CH₂CH₃), 1-hexyl(—CH₂CH₂CH₂CH₂CH₂CH₃), 2-hexyl(—CH(CH₃)CH₂CH₂CH₂CH₃), 3-hexyl(—CH(CH₂CH₃)(CH₂CH₂CH₃)), 2-methyl-2-pentyl(—C(CH₃)₂CH₂CH₂CH₃), 3-methyl-2-pentyl(—CH(CH₃)CH(CH₃)CH₂CH₃), 4-methyl-2-pentyl(—CH(CH₃)CH₂CH(CH₃)₂), 3-methyl-3-pentyl(—C(CH₃)(CH₂CH₃)₂), 2-methyl-3-pentyl(—CH(CH₂CH₃)CH(CH₃)₂), 2,3-dimethyl-2-butyl(—C(CH₃)₂CH(CH₃)₂), 3,3-dimethyl-2-butyl(—CH(CH₃)C(CH₃)₃).

"Aryl" denotes a phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, and like substituents, and which substituents are consistent with the compounds and inclusive of the substituents disclosed in the above mentioned patents or publications for compounds of the formulas (I-XIII).

The term "antibody" herein is used in the broadest sense and specifically covers intact monoclonal antibodies, polyclonal antibodies, multi-specific antibodies (e.g., bispecific antibodies) formed from at least two intact antibodies, and antibody fragments, so long as they exhibit the desired biological activity. An antibody is a protein generated by the immune system that is capable of recognizing and binding to a specific antigen. Described in terms of its structure, an antibody is a Y-shaped protein consisting of four amino acid chains, two heavy and two light. In a simplified model sufficient for this appeal, each antibody has primarily two regions: a variable region and a constant region. The variable region, located on the ends of the arms of the Y, binds to and interacts with the target antigen. This variable region includes a complementary determining region (CDR) that recognizes and binds to a specific binding site on a particular antigen. The constant region, located on the tail of the Y, is recognized by and interacts with the immune system (Janeway, C., Travers, P., Walport, M., Shlomchik (2001) *Immuno Biology, 5th Ed.*, Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The "monoclonal antibodies" may also be isolated from phage antibody libraries using the techniques described in Clackson et al (1991) *Nature*, 352:624-628 and Marks et al (1991) *J. Mol. Biol.,* 222:581-597, for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies of interest herein include "primatized" antibodies comprising variable domain antigen-binding sequences derived from a non-human primate (e.g., Old World Monkey, Ape etc) and human constant region sequences.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Agnew, *Chem Intl. Ed. Engl.,* 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine;

mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); antibodies that have an anti-cancer effect, particularly those that bind to VEGF-1, VEGF-2, VEGF-3, EGF-R, HER-2, CD20, and the like, and pharmaceutically acceptable salts, acids or derivatives of any of the above.

"Het" is a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

"Treat," "treatment," "treating," and like terms refer, in embodiments, to lessen, to eliminate, to inhibit, to improve, to alter, or to prevent a disease or condition, for example by administration of an effective amount of a compound of the present disclosure, or by administration of an effective amount of a compound of the disclosure in combination with an effective amount of an additional chemotherapeutic agent an anti-angiogenic antibody, and can refer to curative therapy, prophylactic therapy, and preventative therapy.

"Modulate," "modulation," "modulating," "modulatory," and like terms refer to, in embodiments, the ability of an effective amount of a compound of the present disclosure to, selectively and at relatively low dose levels, adjust or alter the multi-valent ion (such as calcium ions) permeability of cancerous cells, such as those cells expressing Trp-p8, and in contrast to the relative insensitivity of other cells, for example, healthy or non-cancerous cells and cells not expressing Trp-p8.

"Cancer treatment," "treating cancer," and like terms, for purposes of this disclosure refer, in embodiments, to a method of treating cancer which includes contacting cancer cells with a compound of the disclosure in order to achieve an inhibition of cancer cell growth, a killing of cancer cells, increased patient survival time, or a combination thereof, or contacting cancer cells with a compound of the disclosure in combination with an anti-angiogenic antibody in order to achieve an inhibition of cancer cell growth, a killing of cancer cells, increased patient survival time, an anti-angiogenic effect, or a combination thereof. Treatment of cancer, by the method of the disclosure, also includes contacting the cells with a compound of the disclosure to activate Trp-p8 receptors in cancerous cells, such as tumors, to cause elevated flux levels of multi-valent ions into the cells to cause cell stasis or cell death. Cancer can include diseases in which abnormal cells divide without control. Cancer cells can also invade nearby tissue and can spread through the bloodstream and lymphatic system to other parts of the body. The major categories of cancers are carcinomas, sarcomas, leukemias, and lymphomas. Within these major categories are numerous subgroups that generally describe the organ in which the cancer originates, such as adenocarcinoma of the stomach or oat cell carcinoma of the lung.

"Tumor" refers to, for example, an abnormal benign or malignant mass of tissue that may not be inflammatory, arises from cells of pre-existent tissue, and may possesses no physiological function. Benign tumors, include for example, cysts, warts, moles, and polyps, and generally do not spread to other parts of the body. Malignant tumors are typically composed of cells that grow rapidly, have other abnormal properties that distinguish them from normal cells, and often invade other normal tissues.

"Vascular endothelial cell growth factor," or "VEGF," refers to a mammalian growth factor as defined, for example, in U.S. Pat. No. 5,332,671. The biological activity of native VEGF is shared by any analog or variant thereof that promotes selective growth of vascular endothelial cells but not of bovine corneal endothelial cells, lens epithelial cells, adrenal cortex cells, BHK-21 fibroblasts, or keratinocytes.

"Angiogenic disorder" or "angiogenic defect" refers to an abnormal condition that requires treatment with an agent that inhibits angiogenesis, e.g., an angiostatic compound or composition such as a combination of a compound of the disclosure and an anti-angiogenic antibody. Such disorders include, for example, types of cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, and tumor angiogenesis.

Administration "in combination with" one or more further therapeutic agents includes simultaneous (concurrent) and consecutive administration in any order.

The cool-genic compounds are suitable for use in mammals. As used herein, "mammals" means any class of higher vertebrates that nourish their young with milk secreted by mammary glands, including, for example, humans, horses, cows, pigs, sheep, dogs, rabbits, and monkeys.

"Apoptotic cell death," "programmed cell death," "apoptosis" and like terms refer to any cell death that may result from the complex cascade of cellular events that occur at specific stages of cellular differentiation and in response to specific stimuli. Apoptotic cell death can be characterized by condensation of the cytoplasm and nucleus of dying cells. Apoptosis is an active process requiring new protein synthesis. Typically, the process requires ATP, involves new RNA and protein synthesis, and culminates in the activation of endogenous endonucleases that degrade the DNA of the cell, thereby destroying the genetic template required for cellular homeostasis. Apoptosis is observed in controlled deletion of cells during metamorphosis, differentiation, and general cell turnover, and appears normally to be regulated by receptor-coupled events. For these reasons, apoptosis has been called "programmed cell death" or "cell suicide." While every cell likely has a genetic program to commit suicide, it is usually suppressed. Under normal circumstances, only those cells no longer required by the organism activate this self-destruction program.

"Therapeutically effective amount" means, in embodiments, a dose of a compound of the disclosure, or a dose of a combination of a compound of the disclosure and another chemotherapeutic agent, with or without an excipient, that inhibits, reduces or eliminates tumor growth, in vivo, in vitro, or both, by for example, activating Trp-p8, stimulating apoptosis, or both. The exact dose will depend on the purpose of the treatment, and will be ascertainable by one skilled in the art using known techniques.

In one embodiment of the present disclosure, the compounds of the disclosure are used in combination therapy, for example, with other antibody therapeutic agents. In an embodiment, compounds of the present disclosure are used in combination with known cancer treating antibodies. See generally, for example: PCT/US02/19592; PCT/US01/20118; PCT/US01/25464; PCT/US01/26626; PCT/US02/28859; PCT/US02/41798; PCT/US02/12206; PCT/US03/11148; PCT/US02/12619; and PCT/US02/33050. In another embodiment, compounds of the disclosure are used in combination with an anti-VEGF antibody and like antibodies including human, non-human, murine, hybrid, and chimeric forms. See for example U.S. Pat. No. 6,582,959 (VEGF) and U.S. patent application No. 2002/0,122,797 A1 (human VEGF).

In embodiments of the present disclosure, compounds of the disclosure can be used in combination with other therapeutic agents, such as the antibodies noted above, to treat immunological diseases or conditions, for example, involving immune responsive cells such as B-cells (B lymphocytes), T-cells (T lymphocytes), accessory cells (macrophages and other antigen-presenting cells), killer cells (NK and K cells), mast cells, and like cells.

In a preferred embodiment, compounds useful in the present disclosure include a non-radio labeled compound for treatment of non-central nervous system cells or diseases. In embodiments, compounds of the present disclosure do not contain a radio-label and are not radio-active. The unlabeled compounds of the present disclosure can be used to kill cancer cells as illustrated herein, for example, cells expressing Trp-p8, such as prostate cancer cells and liver cancer cells.

A "subject" for the purposes of the present disclosure includes both humans and other animals, particularly mammals. Thus, the methods are applicable to both human therapy and veterinary applications. In a preferred embodiment the subject is a mammal, and in the most preferred embodiment the subject is human.

"Improved therapeutic outcome" or "decrease in the number of tumor cells" or "decreased tumor size" means a 50% decrease, preferably an 80% decrease, more preferably a 90% decrease, and even more preferably a 100% decrease in the tumor size or volume, a decrease in the number of detectable circulating cancer cells in the blood, affected tissue, or organ as determined by examination of a patient, samples taken from a patient prior to and following treatment, or both.

"Compound," "molecule," "polypeptide," and like terms include synthetically prepared compounds, genetically engineered compounds (e.g., recombinant DNA expressed proteins), naturally occurring compounds, and those produced in vivo after administration of a different compound. The in vivo effects of administered compounds described herein may not be exerted by those compounds as such, but by one or more degradation products, such as a metabolite, conjugate, clathrate, ion complex, chelate, hydrate, solvate, or like biological transformations or combinations, of the administered compound(s) or molecule(s). "Pharmaceutically acceptable salts" can also include, in addition to those illustrated herein, a subclass of salts present or formed in vivo.

The present disclosure provides compounds that bind to certain receptors in the TRP (transient receptor potential) ion channel family. More particularly the present disclosure provides compounds that specifically bind to the subgroup of long TRP (or TRPM) channels, and most particularly to compounds that specifically bind to the TRP channel called "Trp-p8" (or TRP-M8). The Trp-p8 receptors are typically present at elevated levels in cancers, such as prostate cancer. The compounds of the disclosure are endowed with Trp-p8 receptor activating activity. Activation of the Trp-p8 receptor causes increased calcium ion flow into cancerous cells and ultimately cell death. Compounds of the present disclosure are useful for, but not limited to, the treatment of cell proliferation diseases or disorders, and stimulating apoptosis. It is also well known in the art and as illustrated herein how to determine Trp-p8 receptor activity, for example, using the standard tests described herein, or using other similar tests.

It will be appreciated by those skilled in the art that compounds of the disclosure having a chiral center may exist in and be isolated in optically active and racemic forms. Some compounds may exhibit polymorphism. It is to be understood that the present disclosure encompasses any racemic, optically-active, polymorphic, tautomeric, or stereoisomeric form, or mixture thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase). In particular, it is understood that compounds of the disclosure, such as of formulas (I-XIII), can contain chiral centers, for example, in the R₁ substituents of formula (I), the R₃ substituents of formula (V), and in the R₁ to R₆ substituents of formula (XIII). It is also understood that compounds of the disclosure, such as formula (I), can exist in the "enol" form or the corresponding tautomeric "keto" form, and that all such tautomers are included as compounds within the scope of the present disclosure.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-6}$alkyl or ($C_1$-$C_6$)alkyl refers to alkyl of one to six carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the disclosure include compounds of formula (I-XIII) having any combination of the values, specific values, more specific values, and preferred values described herein.

Specifically, aryl can be phenyl, naphthyl, anthracenyl, phenanthrenyl, fluorenyl, tetrahydronaphthyl, or indanyl.

Specifically, alkyl such as ($C_{1-6}$)alkyl can be methyl, ethyl, propyl, isopropyl, butyl, iso-butyl, sec-butyl, tert-butyl, pentyl, 3-pentyl, hexyl, or heptyl; ($C_2$-$C_6$)alkyl, can be ethyl, propyl, isopropyl, butyl, iso-butyl, sec-butyl, tert-butyl, pentyl, 3-pentyl, or hexyl; ($C_{3-12}$)cycloalkyl can be cyclopropyl, cyclobutyl, cyclopentyl, cyclohexyl, cycloheptyl, cyclooctyl, bicyclic, or multi-cyclic substituents, such as of the formulas

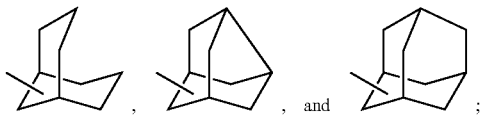

$C_{1-6}$alkoxy can be methoxy, ethoxy, propoxy, isopropoxy, butoxy, iso-butoxy, sec-butoxy, pentoxy, 3-pentoxy, or hexyloxy; —C(═O)alkyl or ($C_2$-$C_7$)alkanoyl can be acetyl, propanoyl, butanoyl, pentanoyl, 4-methylpentanoyl, hexanoyl, or heptanoyl; aryl can be phenyl, indenyl, or naphthyl; Het can be pyrrolidinyl, piperidinyl, morpholinyl, thiomorpholinyl, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thienyl, pyrimidinyl (or its N-oxide), indolyl, isoquinolyl (or its N-oxide) or quinolyl (or its N-oxide).

A specific value for Het is a five-(5), six-(6), or seven-(7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic Het diradical thereto.

A specific compound of formula (I) is a compound of the Formula (A)

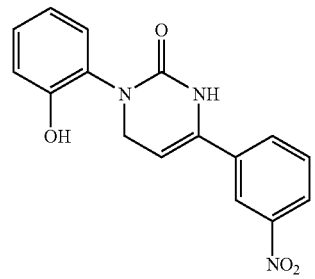

A (Icilin, also known as AG-3-5).

A specific compound of formula (II) is a compound of the Formula (B)

B(IIa3-1)

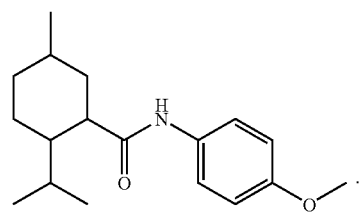

Another specific compound of formula (II) is a compound of the Formula (C) showing a preferred stereochemistry:

C(IIa4-1)

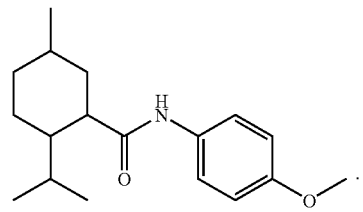

Another specific compound of formula (II) is a compound of the Formula (D):

D(IIb-1)

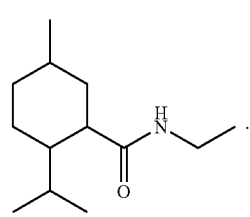

A specific compound of formula (III) is a compound of the Formula (E):

E(III-1)

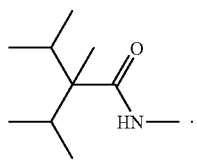

A specific compound of formula (IV) is a compound of the Formula (F):

F(IV-1)

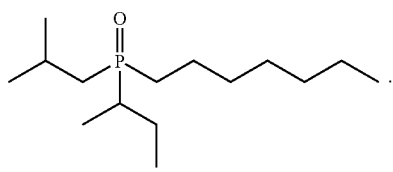

A specific compound of formula (V) is a compound of the Formula (G):

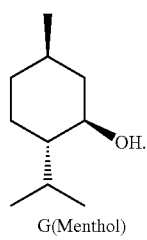

G(Menthol)

A specific compound of formula (VI) is a compound of the Formula (H):

H(VI-1)

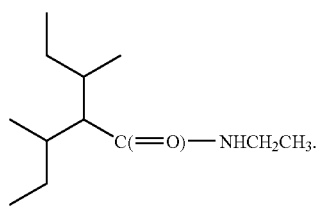

A specific compound of formula (VII) is a compound of the Formula (I'):

I'(VII-1)

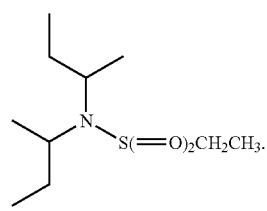

A specific compound of formula (IX) is a compound of the Formula (J):

J(IX-1)

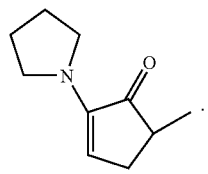

A specific compound of formula (X) is a compound of the Formula (K):

K(X-1)

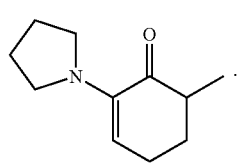

A specific compound of formula (XI) is a compound of the Formula (L):

L(XI-1)

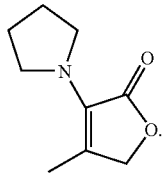

A specific compound of formula (XII) is a compound of the Formula (M):

M(XII-1)

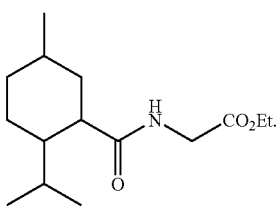

A specific compound of formula (XIII) is a compound of the Formula (N):

N(XIII-1)

It is understood that the abovementioned specific compounds of the Formulas (A-N), and all other compounds of the disclosure, can be or include a pharmaceutically acceptable salt thereof.

A specific compound is 3-(2-Hydroxy-phenyl)-6-(3-nitro-phenyl)-3,4-dihydro-1H-pyrimidin-2-one; or a pharmaceutically acceptable salt thereof.

Another specific compound is 2-Isopropyl-5-methyl-cyclohexanecarboxylic acid(4-methoxy-phenyl)-amide; or a pharmaceutically acceptable salt thereof.

Another specific compound is 2-Isopropyl-2,3,-N-trimethyl-butyramide; or a pharmaceutically acceptable salt thereof.

Another specific compound is 1-(sec-Butyl-isobutyl-phosphinoyl)-heptane; or a pharmaceutically acceptable salt thereof.

Another specific compound is 2-Isopropyl-5-methyl-cyclohexanol; or a pharmaceutically acceptable salt thereof.

A specific compound of formula IIa is a compound of the formula IIa1:

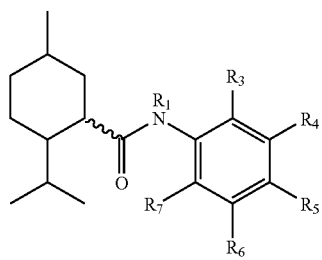

IIa1 or a pharmaceutically acceptable salt thereof; wherein $R_1$, $R_3$, $R_4$, $R_5$, $R_6$, and $R_7$ are as defined herein.

Other specific compounds of formula IIa are individual compounds of the formulas IIa2-IIa12, or a pharmaceutically acceptable salt thereof; wherein the R substituents are as defined herein:

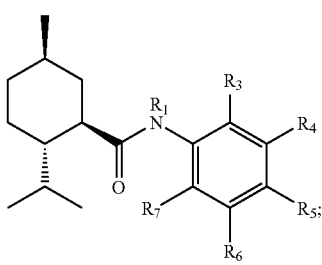

IIa2

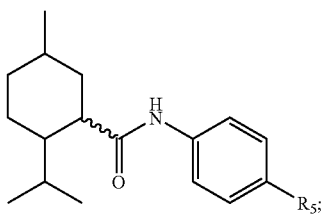

IIa3

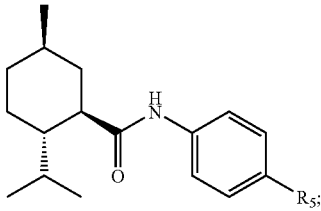

IIa4

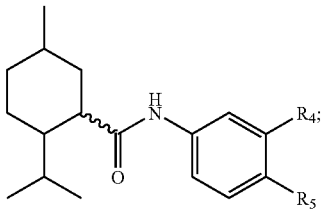

IIa5

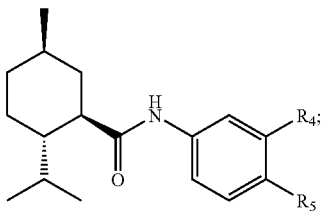

IIa6

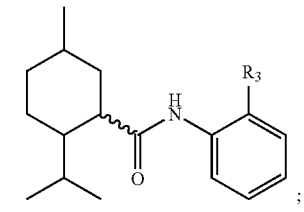

IIa7

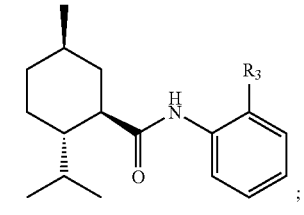

IIa8

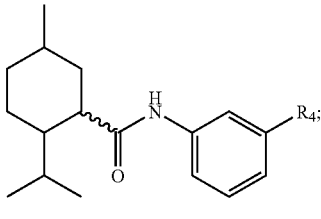

IIa9

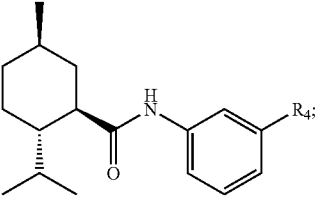

IIa10

-continued

IIa11

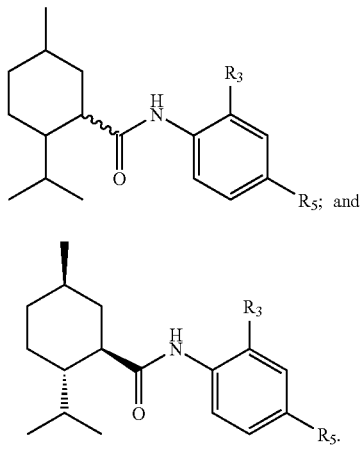

R5; and

IIa12

Specific compounds of formula IIa include:

2-Isopropyl-5-methyl-cyclohexanecarboxylic acid (4-morpholin-4-yl-phenyl)-amide, or a pharmaceutically acceptable salt thereof;

2-Isopropyl-5-methyl-cyclohexanecarboxylic acid(3-chloro-4-methoxy-phenyl)-amide, or a pharmaceutically acceptable salt thereof;

2-Isopropyl-5-methyl-cyclohexanecarboxylic acid(4-sec-butyl-phenyl)-amide, or a pharmaceutically acceptable salt thereof;

2-Isopropyl-5-methyl-cyclohexanecarboxylic acid indan-5-ylamide, or a pharmaceutically acceptable salt thereof;

2-Isopropyl-5-methyl-cyclohexanecarboxylic acid(4-tert-butyl-phenyl)-amide, or a pharmaceutically acceptable salt thereof;

2-Isopropyl-5-methyl-cyclohexanecarboxylic acid(4-propyl-phenyl)-amide, or a pharmaceutically acceptable salt thereof; and 2-Isopropyl-5-methyl-cyclohexanecarboxylic acid(4-isopropyl-3-methyl-phenyl)-amide, or a pharmaceutically acceptable salt thereof.

Preparative procedures, characterization, cool-genic properties, odor properties, structure-coolgenic activity relationships, design rules, and like information for compounds of the formulas (I-XIII) and for the above mentioned specific compounds of formulas A-N are reported in the corresponding above mentioned publications or patents.

Compounds of the disclosure, such as compounds of formulas B, C, D or N can be prepared as illustrated, for example, in the scheme below, by procedures analogous thereto, by procedures in the above mentioned publications or patents, or by procedures which are known or would be readily evident to one of ordinary skill in the art. All of the variables used in the schemes are as defined below or elsewhere herein. Scheme 1 illustrates the preparation of representative compounds of the disclosure, such as amide compound 3 (IIa4-1). Chloro compound 1 was carboxylated via a Grignard intermediate to afford carboxylic acid 2 and the acid 2 was converted to the amide 3 and as described in Example 1 herein.

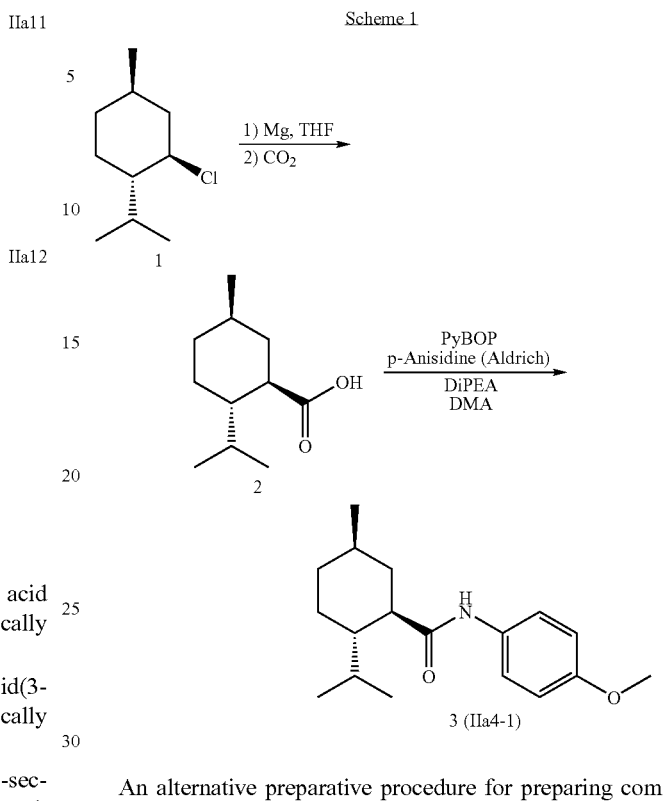

An alternative preparative procedure for preparing compound 3 (IIa4-1) and related amide compounds uses the corresponding acid chloride of the above mentioned carboxylic acid compound 2. The acid chloride of carboxylic acid compound 2 (readily prepared by reaction with $SOCl_2$ and like reagents) can be reacted with a variety of primary or secondary amine compounds to form the corresponding amides analogous to amide 3. Other compounds related to amide 3 or formula II, were similarly prepared and as illustrated and described herein.

For a synthetic procedure for making menthanecarboxylic acid compound 2 (a starting material for IIa4-1), see D. G. Rowsell, Wilkinson Sword Ltd., U.K. Patent (1975) in the listing mentioned below. For another synthetic procedure for making the menthanecarboxylic acid, see D. Cunningham, et. al., *J. Chem. Soc., Perkin Trans. I,* 2002, 2692-2698.

For additional preparative details for making cool-genic compounds mentioned in *J. Soc. Cosmet. Chem.,* 1978, 29, 185-200, see on page 199, reference 1, listing of 17 U.K. Patents.

Other conditions suitable for formation of the compounds of the disclosure from a variety of intermediates as illustrated herein are well known to the art. For example, see Feiser and Feiser, "Reagents for Organic Synthesis," Vol. 1, 1967; March, J. "Advanced Organic Chemistry," $4^{th}$ ed., John Wiley & Sons, 1992; House, H. O., "Modem Synthetic Reactions", $2^{nd}$ ed., W. A. Benjamin, New York, 1972; and Larock, R. C., "Comprehensive Organic Transformations," $2^{nd}$ ed., Wiley-VCH Publishers, New York, 1999.

The starting materials employed in the synthetic methods described herein are commercially available, have been reported in the scientific literature, or can be prepared from readily available starting materials using procedures known in the field. It may be desirable to optionally use a protecting group during all or portions of the above described or alternative synthetic procedures. Such protecting groups and methods for their introduction and removal are well known in the art. See Greene, T. W.; Wutz, P. G. M. "Protecting Groups In Organic Synthesis" $2^{nd}$ ed., New York, John Wiley & Sons, Inc., 1991.

In cases where compounds are sufficiently basic or acidic to form stable nontoxic acid or base salts, administration of the compound of the disclosure as a salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metals, for example, sodium, potassium or lithium, or alkaline earth metal salts, for example, calcium, of carboxylic acids can also be made.

Compounds of the present disclosure can conveniently be administered in a pharmaceutical composition containing the compound in combination with a suitable excipient, the composition being useful in treating tumors. Pharmaceutical compositions containing a compound appropriate for antitumor use are prepared by methods and contain excipients well known in the art. A generally recognized compendium of such methods and ingredients is Remington's Pharmaceutical Sciences by E. W. Martin (Mark Publ. Co., $15^{th}$ ed., 1975). The compounds and compositions of the present disclosure can be administered parenterally, for example, by intravenous, intraperitoneal or intramuscular injection, orally, or rectally, depending on, for example, the disposition or dissemination of the tumor cells.

In embodiments, the antibodies included within the scope of the disclosure include hybrid and recombinant antibodies (e.g., "humanized" and "human" antibodies) regardless of species of origin or immunoglobulin class or subclass designation, as well as antibody fragments (for example, Fab, F(ab')$_2$, and F$_v$). See U.S. Pat. No. 4,816,567; Mage and Lamoyi, in *Monoclonal Antibody Production Techniques and Applications*, 79-97, Marcel Dekker, Inc., New York, (1987).

Thus, the modifier "monoclonal" indicates the character of the antibody as being obtained from such a substantially homogeneous population of antibodies, and is not to be construed as requiring production of the antibody by any particular method. For example, the monoclonal antibodies of the disclosure may be made using the hybridoma method first described by Kohler & Milstein, *Nature*, 256:495 (1975), or may be made by recombinant DNA methods. See U.S. Pat. No. 4,816,567. Other known methods of antibody production are described, for example, in Goding, *Monoclonal Antibodies: Principles and Practice*, 59-103, Academic Press (1986); Kozbor, *J. Immunol.*, 133:3001 (1984). Brodeur, et al., *Monoclonal Antibody Production Techniques and Applications*, 51-63, Marcel Dekker, Inc., New York (1987).

Various methods have been employed to produce monoclonal antibodies (MAbs). Hybridoma technology, which refers to a cloned cell line that produces a single type of antibody, uses the cells of various species, including mice (murine), hamsters, rats, and humans. Another method to prepare MAbs uses genetic engineering including recombinant DNA techniques. Monoclonal antibodies made from these techniques include, among others, chimeric antibodies and humanized antibodies. A chimeric antibody combines DNA encoding regions from more than one type of species.

For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

As noted, murine antibodies play an important role in these technologies. While useful for diagnostics and short-term therapies, murine antibodies cannot be administered to people long-term without increasing the risk of a deleterious immunogenic response. This response, called Human Anti-Mouse Antibody (HAMA), occurs when a human immune system recognizes the murine antibody as foreign and attacks it. A HAMA response can cause toxic shock or even death.

Chimeric and humanized antibodies reduce the likelihood of a HAMA response by minimizing the nonhuman portions of administered antibodies. Furthermore, chimeric and humanized antibodies have the additional benefit of activating secondary human immune responses, such as antibody dependent cellular cytotoxicity.

"Antibody fragments" comprise a portion of an intact antibody, preferably comprising the antigen-binding or variable region thereof. Examples of antibody fragments include Fab, Fab', F(ab')2, and Fv fragments; diabodies; linear antibodies; single-chain antibody molecules; and multi-specific antibodies formed from antibody fragment(s).

An "intact" antibody is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

When used in vivo for combination therapy, antibodies can be administered to the patient in therapeutically effective amounts (i.e. amounts that eliminate or reduce the patient's tumor burden). The combination of a compound of the disclosure and antibodies can be administered at the same time or sequentially. They will normally be administered parenterally, when possible, at the target cell site, or intravenously. The dose and dosage regimen will depend upon, for example, the nature of the cancer (primary or metastatic), its population, the site to which the antibodies are to be directed, the characteristics of the particular immunotoxin (when used), for example, its therapeutic index, the patient, and the patient's history. The amount of antibody administered will typically be in the range of about 0.1 to about 10 mg/kg of patient weight. The amount of a compound of the disclosure administered in combination with an antibody can typically be, for example, in the range of about 5 to 1,000 mg, or about 0.1 to 300 mg/kg of patient body weight, and can depend on many of the abovementioned factors and considerations.

The present disclosure also contemplates using combinations of a compound of the disclosure with an anti-TRP-P8 antibody in diagnostic applications. For diagnostic applications, the antibodies of the disclosure typically will be labeled with a detectable moiety. The detectable moiety can be any one capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for separately conjugating the antibody to the detectable moiety may be employed, including those methods described by Hunter, et al., *Nature*, 144: 945 (1962); David, et al., *Biochemistry*, 13:1014 (1974); Pain, et al., *J. Immunol. Meth.*, 40:219 (1981); and Nygren, *J. Histochem. and Cytochem*, 30:407 (1982).

For therapeutic applications, antibodies may be administered to a mammal, preferably a human, in a pharmaceutically acceptable dosage form, including those that may be administered to a human intravenously as a bolus or by continuous infusion over a period of time, by intramuscular, subcutaneous, intra-articular, or inhalation routes. An antibody is also suitably administered by intra-tumoral, peritumoral, intralesional, or peri-lesional routes, to exert local as well as systemic therapeutic effects.

Such dosage forms encompass known pharmaceutically acceptable carriers or vehicles that are inherently nontoxic and non-therapeutic. An antibody will typically be formulated in such vehicles at a concentration of about 0.1 mg/ml to 100 mg/ml.

For the prevention or treatment of disease, the appropriate dosage of a combination of a compound of the disclosure will depend on the type of disease to be treated, as defined above, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments.

Depending on the type and severity of the disease, about 0.015 to 15 mg/kg of the compound is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful.

For oral therapeutic administration, the active compound of the disclosure may be combined with one or more excipients and used in the form of ingestible tablets, buccal tablets, troches, capsules, elixirs, suspensions, syrups, wafers, and the like. Such compositions and preparations typically contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar, and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions of the disclosure can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes or implantable seeds or pellets. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum-drying and freeze-drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. Useful dosages of the compounds of the disclosure can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1,000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

For internal administration, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1,000 mg per unit dose.

For parenteral administration or for administration as drops, as for eye treatments, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula (I-XIII) in a liquid composition, such as an IV (intravenous), will be from about 0.1 to about 25, preferably from about 0.5 to about 10, weight percent. The concentration in a semi-solid or solid composition such as a gel or a powder will be about 0.1 to about 5 weight percent, preferably about 0.5 to about 2.5 weight percent.

The exact regimen for administration of the compounds and compositions disclosed herein will necessarily be dependent upon the needs of the individual subject being treated, the type of treatment and, of course, the judgment of the attending practitioner.

The binding activity and binding selectivity of the compounds of the present disclosure are excellent predictors of the anti-tumor activity of compounds of the disclosure. The binding activity and binding selectivity can be determined using pharmacological models well known to the art, or using the assays described below. Exemplary results of biological testing are summarized in Table 1 below.

Evaluation of Biological Activity

General methods and materials disclosed in R. Skyryma, et al., *J. Physiology*, 2000, 527.1, 71-83, for assessing and measuring calcium ion flux or cell uptake, and induction of apoptosis were adapted for use in the present disclosure and as illustrated herein. Other test methods and procedures such as described below, including cell line culturing, transfection, and in vivo and in vitro tumor growth inhibition, are readily apparent to one of ordinary skill in the art upon comprehending the disclosure.

Assays for Activity

For cancer, a variety of well-known animal models can be used to further understand the role of the genes in the development and pathogenesis of tumors, and to test the efficacy of candidate therapeutic agents, including combinations of compounds of the disclosure and anti-angiogenic antibodies. The in vivo nature of such models makes them particularly predictive of responses in human patients. Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See for example, PCT publication No. WO 97/33551, published Sep. 18, 1997.

Probably the most often used animal species in oncological studies are immunodeficient mice and, in particular, nude mice. The observation that the nude mouse with thymic hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumor xenografts. For further details see for example, *The Nude Mouse in Oncology Research*, E. Boven and B. Winograd, eds. (CRC Press, Inc., 1991).

The cells introduced into such animals can be derived from known tumor/cancer cell lines, such as any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); or a moderately well-differentiated grade II human colon adenocarcinoma cell line, HT-29 (ATCC HTB-38); or from tumors and cancers. Samples of tumor or cancer cells can be obtained from patients undergoing surgery, using standard conditions involving freezing and storing in liquid nitrogen. Karmali et al., *Br. J. Cancer,* 48: 689-696 (1983). Tumor cells can be introduced into animals such as nude mice by a variety of procedures. The subcutaneous (s.c.) space in mice is very suitable for tumor implantation. Tumors can be transplanted s.c. as solid blocks, as needle biopsies by use of a trochar, or as cell suspensions. For solid-block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin, et al., *Proc. Nat. Acad. Sci. USA,* 83: 9129-9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang, et al., *Cancer Research*, 54: 4726-4728 (1994) and Too, et al., *Cancer Research*, 55: 681-684 (1995). This model is based on the so-called "METAMOUSE"™ sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines. The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

EXAMPLE 1

Preparation of Compound IIa4-1 from (−)Menthyl chloride. 1.39 grams of Mg metal (57 mmol) was placed in a 100 mL flask and 4 mL of dry THF was added to cover the Mg metal. A crystal of iodine was added to the metal-THF mixture and stirred for several minutes followed by the addition of about ⅓ portion of 10 grams (57 mmol) of (−)menthyl chloride (Aldrich). The mixture was heated to induce Grignard formation and the remaining menthyl chloride (⅔portion) was added in 50 mL dry THF and stirred until the reaction was complete. The Grignard solution was then canulated under nitrogen into a vessel containing excess dry ice. This dry ice quenched mixture was swirled and poured into 300 mL ice containing 2 mL concentrated HCl. Diethyl ether was added and the mixture separated. The separated organic layers were combined and washed with water then extracted with an aqueous NaOH solution. The aqueous solution (and oil) was acidified with HCl until a solid formed, diethyl ether was added, and the acid was extracted into the organic phase, washed with brine, dried over sodium sulfate, and concentrated to give 4.18 grams (40%) as white needles.

The acid (0.57 grams, 3.1 mmol) was dissolved in 1.5 mL dimethylacetamide (DMA). The PyBOP (2.1 grams, 4.0 mmol), p-anisidine (0.58 grams, 4.7 mmol, Aldrich) and DiPEA (2.7 mL, 15.5 mmol) were added. Another 0.25 grams p-anisidine was added after 2 hours and again after 5 hours. The reaction was diluted with ethyl acetate (EtOAc) after 7 hours, washed twice with 1 N HCl, twice with aqueous sodium bicarbonate, and then with brine. The separated organic layers were combined and dried over sodium sulfate and concentrated to a brown solid. This solid was put through a plug of silica gel with 30% EtOAc/hexanes to remove the color. The product began to crystallize upon concentration, so the crystallization was allowed to occur, the solvent was removed by pipette, and the white needles were washed with cold EtOAc and dried under vacuum to give 0.365 grams (1.26 mmol, 40% yield) of a first crop. Recrystallization of the mother liquor yielded an additional 0.346 grams (1.2 mmol, 39% yield) as white needles.

LCMS showed the product to have a molecular weight of 289, corresponding to the desired molecular weight, and the NMR spectra showed it to have the desired structure.

EXAMPLE 2

Demonstration of Ion Channel Activity in Response to Selected Cool-Genic Compounds—Calcium Ion Uptake Evaluation. Calcium ion uptake experiments were conducted as follows. Calcium uptake was measured for cells expressing Trp-p8 tumor antigen and for cells not expressing Trp-p8 tumor antigen after each cell line was contacted with cool-genic compounds of the present disclosure. The results showed that cells expressing Trp-p8 tumor antigen had progressively increased calcium uptake as the concentration of cool-genic compound was increased incrementally over about five concentration decades from about 0.0001 to about 10 microM. Compound (IIa4-1) had unexpectedly particularly high calcium uptake at all cool-genic compound concentrations. Cells not expressing tumor antigen had essentially no observable calcium uptake over all of the cool-genic compound concentrations. Dimethyl sulfoxide (DMSO), a non-coolgenic compound, was used as a control compound in both expressing and non-expressing cell lines and which DMSO exposed cells showed no appreciable calcium uptake at any concentration. Cell lines included non-expressing lines: 293, PC3, and PC3/neo; and tumor antigen expressing lines: 293, PC3, and PC3/neo.

EXAMPLE 3

Figure 1B:
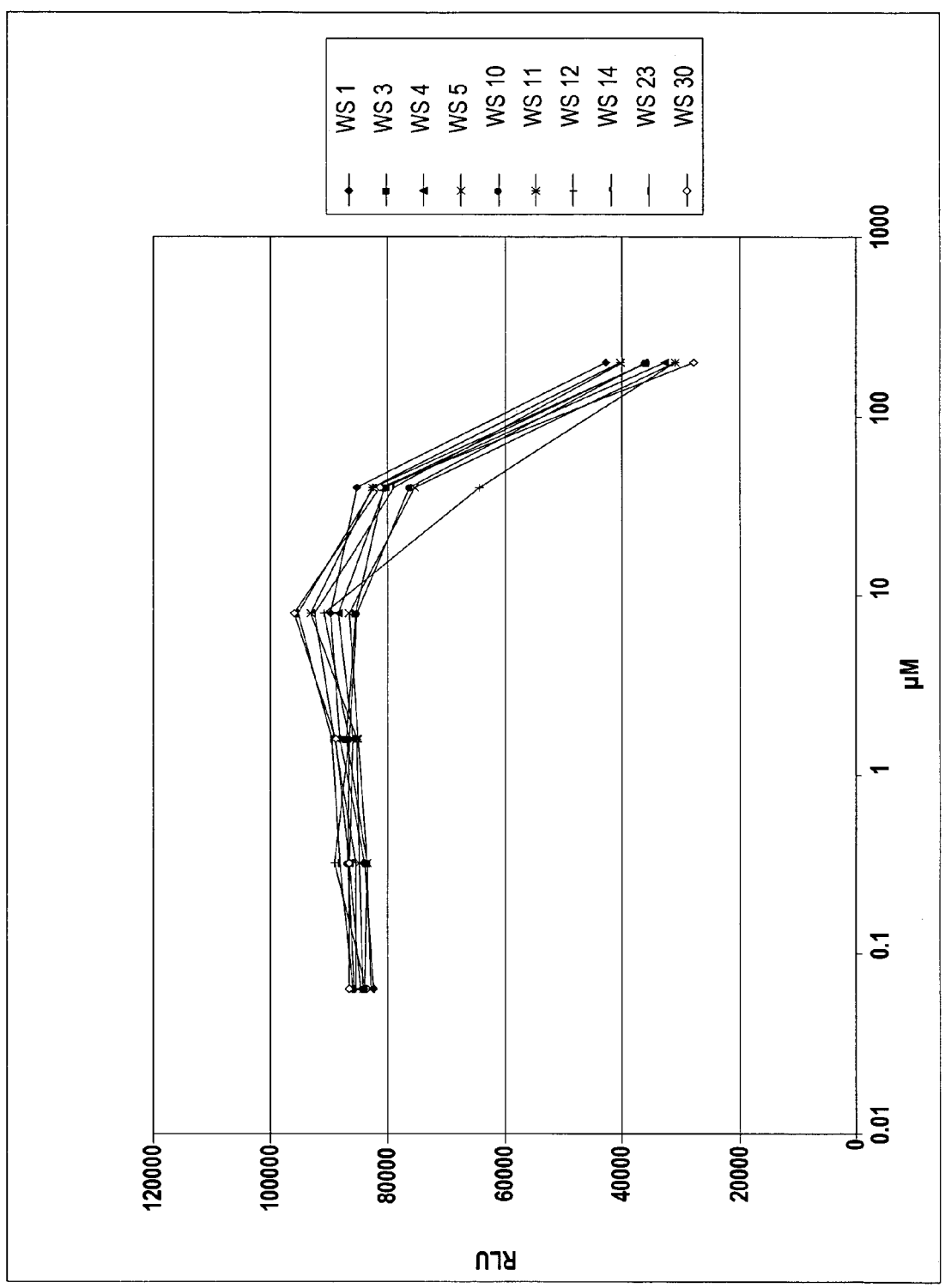
Figure 1C:
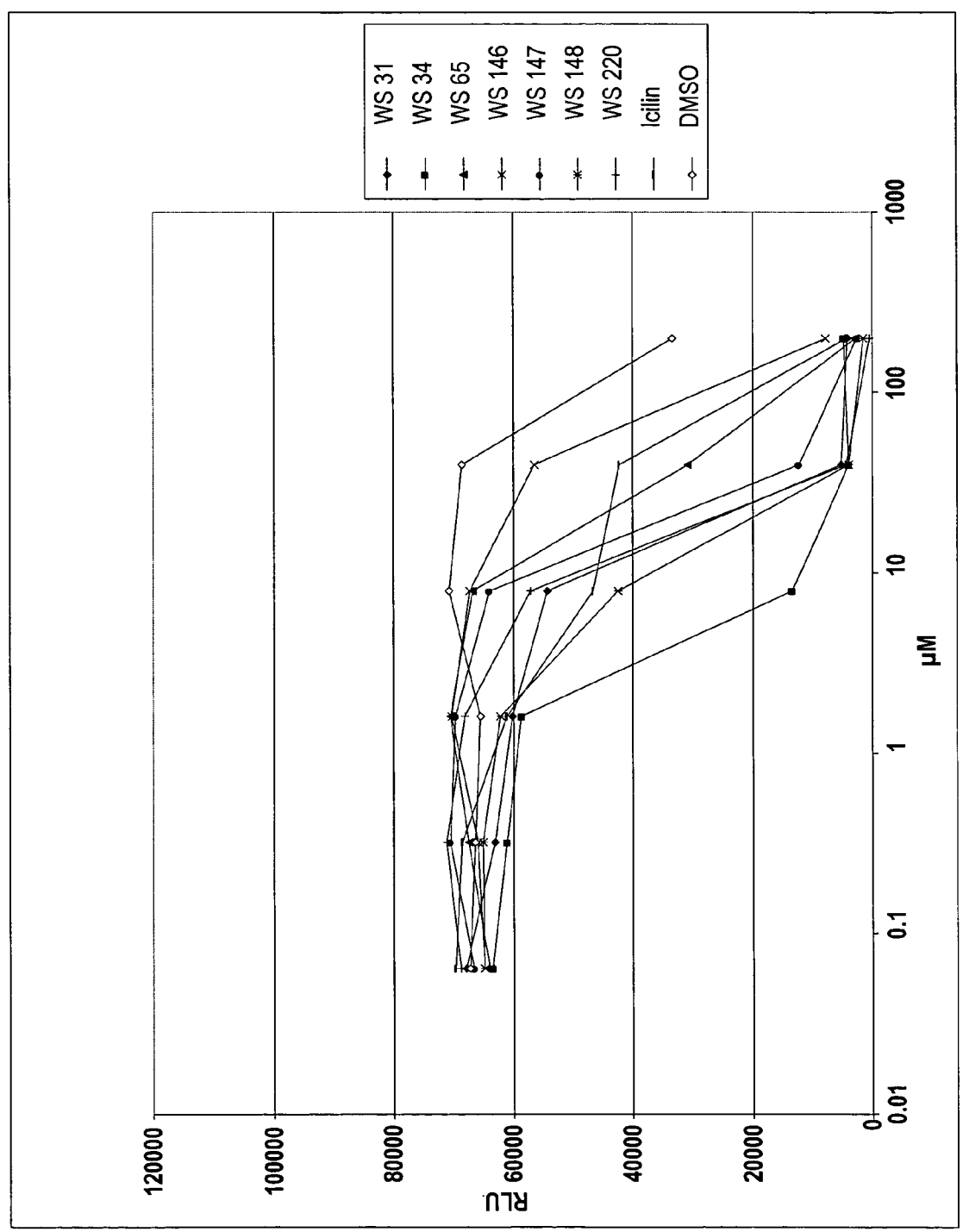
Figure 1D:
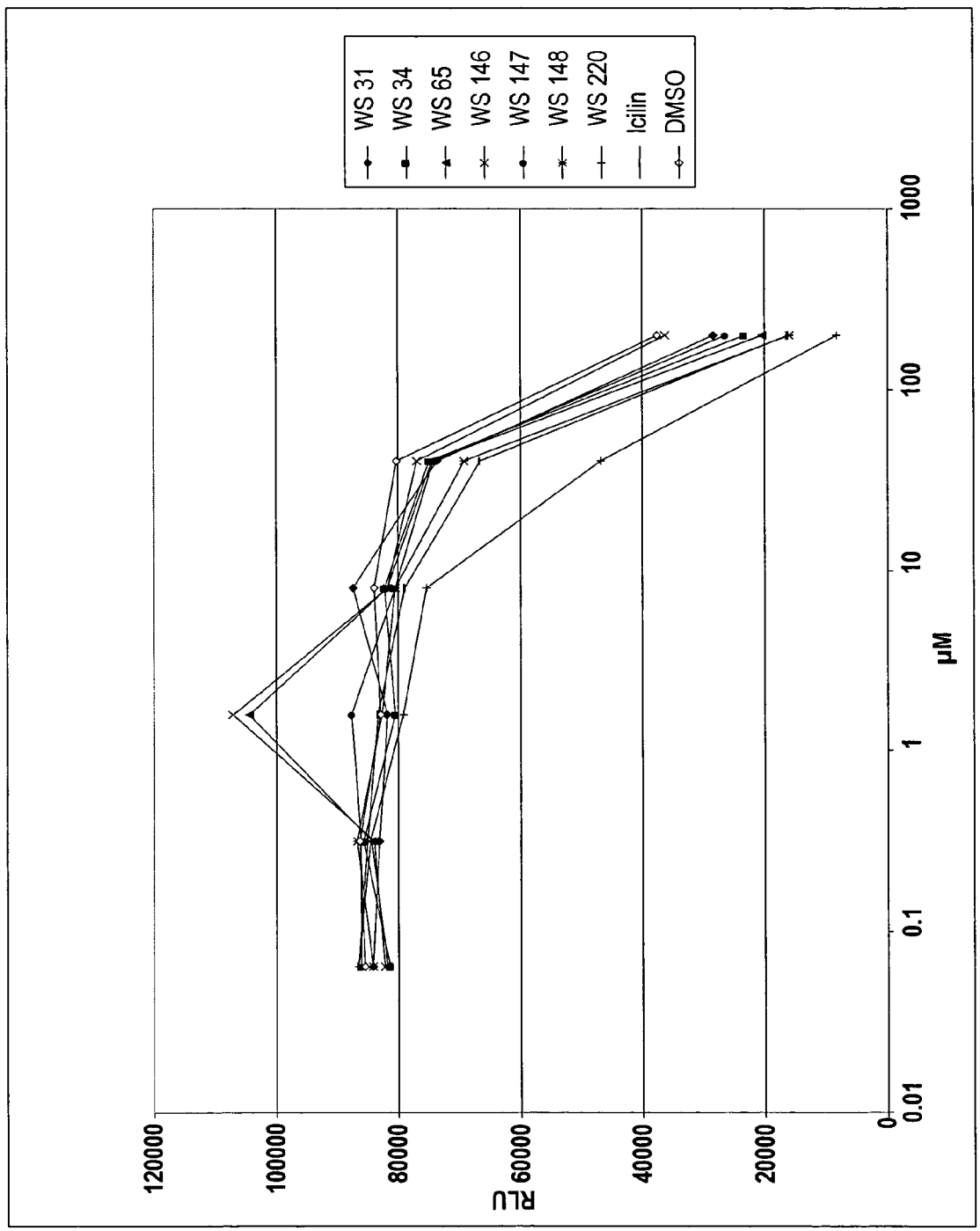

Human Cell Killing in vitro by Compounds that Activate Trp-p8. Referring to the Figures, in FIG. 1 the effectiveness of selected cool-genic compounds in human cell killing was evaluated. The order and potency of cool-genic compounds were compared in two related human cell lines, one was 293 cells expressing Trp-p8 and a second was matched 293 cells lacking (not expressing) Trp-p8 used as a control. There were about 50,000 cells per well at plating. The cool-genic compounds were added at plating. The cells were treated by exposing the cells to the individual compounds at varying concentrations over about 0.1 to about 1,000 microM for 72 hours. The x-axis shows concentration increments and the y-axis shows the number (in arbitrary units) of viable cells remaining at the end of 72 hours. FIGS. 1A and 1C show the response of cells expressing Trp-p8 and treated with the indicated numbered or named coolgenic compounds. FIGS. 1B and 1D show the response of cells without (not expressing) Trp-p8 and also treated with the indicated coolgenic compounds. The results in FIGS. 1A and 1C show that the cells with Trp-p8 had a range of kill responses or potencies with respect to the coolgenic compounds. Compound IIa4-1 had the best kill ($IC_{50}$<1 microM) for cells expressing Trp-p8. The comparative results in FIGS. 1B and 1D show that the cells without Trp-p8 had a lower or essentially no kill response to the same coolgenic compounds, particularly at the lower concentrations of the coolgenic compounds, e.g., below 100 microMolar.

EXAMPLE 4

Figure 2:
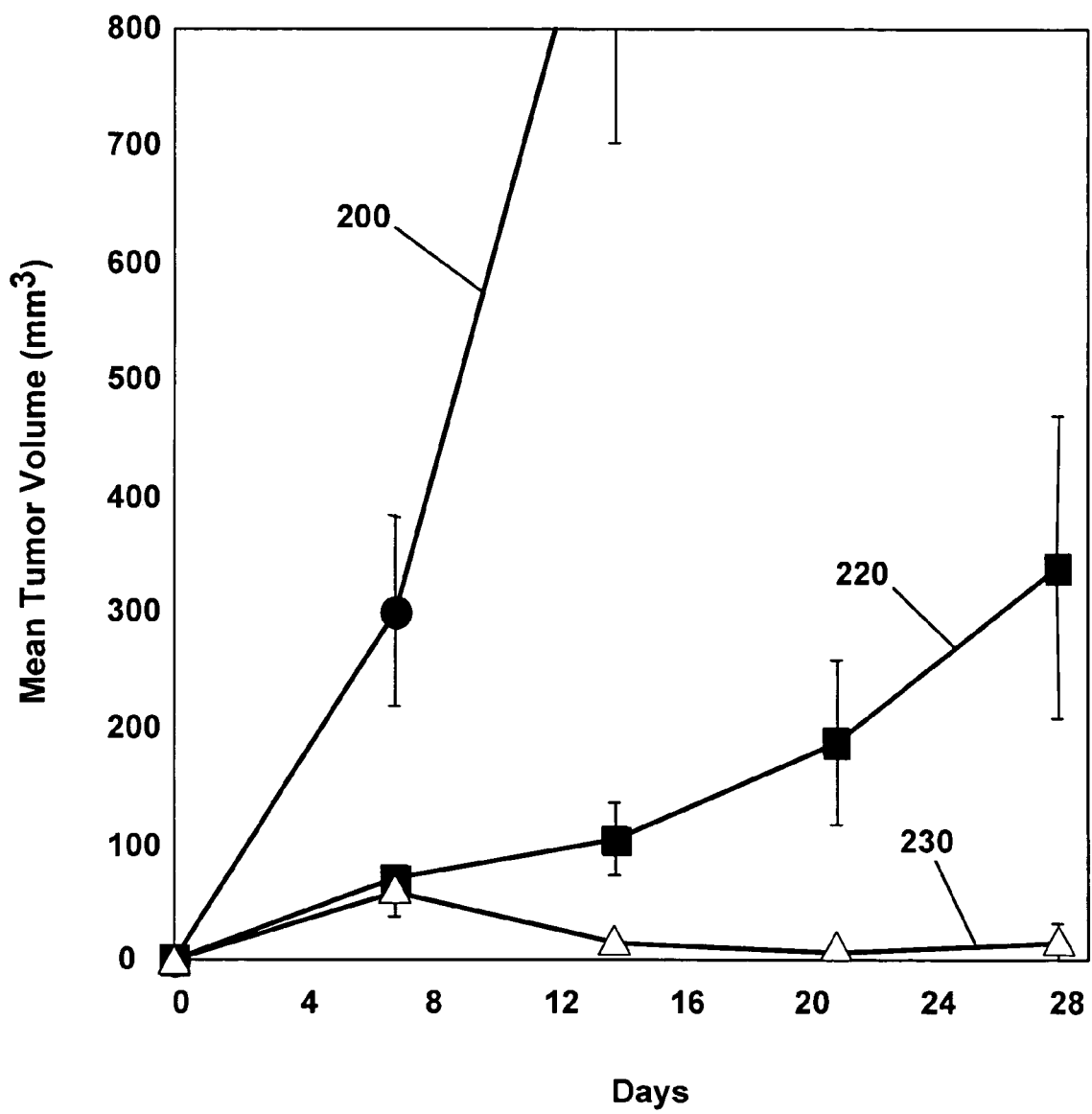
FIG. 2 illustrates the relative growth rates for cloned cancerous cell lines (PC3/Trp-p8) which express Trp-p8 compared to a control cell line (PC3-Neo) which does not express Trp-p8.

Procedure for inhibition of tumor growth in vivo by compounds that activate Trp-p8. Methods for preparing transfected cancerous cells, such as those expressing Trp-p8, is readily apparent to one of ordinary skill in the art, see for example J. M. Schallhorn, et al., *Nucleic Acids Res., Feb.* 15, 1996;24(4):596-601. Referring to the FIG. 2, there is illustrated the growth of PC3 clone cells transfected to express tumor antigen, (PC3/Trp-p8.c8 and .c9), and PC3 clone cells not expressing tumor antigen (PC3-Neo) in athymic nude mice (5 million cells/mouse). The non-Trp-p8 expressing tumor forming human prostate cancer cell line, PC3-Neo 200 (-●-), shows expected exponential tumor cell growth rates. In contrast, the Trp-p8 expressing (i.e. "over-expressing") tumor forming human prostate cancer cell lines, PC3/Trp-p8:

.c8 (clone 8) 220 (-■-); and .c9 (clone 9) 230 (-▲-), show substantially slower growth and static growth rates, respectively.

Athymic mice (8 per group) are inoculated in the flank with about $5\times10^6$ of PC3 clone cells stably expressing Trp-p8 (cl.8) or a vector control cell line (PC3-Neo). Tumors are established to a size of approximately 200 mg each at which time coolgenic compounds are administered once or twice per day I.V. or P.O. at doses ranging from about 1-30 mg/kg body weight. Tumor volumes are measured by caliper every third day and average volumes are calculated.

Contacting, in vivo, the Trp-p8 expressing cancerous cells, such as those illustrated above, with certain coolgenic compounds of moderate to high potency of the present disclosure, and as illustrated herein, is expected to result in high cell kill for Trp-p8 expressing cancerous cells and no cell kill or low cell kill for healthy or non-Trp-p8 expressing cells. This expectation is consistent with the abovementioned in vitro human cell killing results presented in EXAMPLE 3.

Table 1 summarizes exemplary ion channel activity and Cell Kill response to selected cool-genic compounds, mentioned above or illustrated below, and provides a comparative or relative activity ranking for those compounds.

TABLE 1

Ion Channel Activity and Cell Killing in Response to Selected CoolGenic Compounds.

| Activity Ranking | Compound ID# | Peak (FLIPR)[1] | 293/Trp-p8 Cell Killing | PC3/Trp-p8 Cell Killing |
|---|---|---|---|---|
| 1 | IIa4-1 | 31,000 | Yes | Yes |
| 2 | IV-1 | 31,000 | Yes | |
| 3 | XIII-1 | 29,000 | Yes | Yes |
| 4 | IV-2 | 29,000 | | |
| 5 | IIb-2 | 25,100 | Yes | Yes |
| 6 | IIb-3 | 25,100 | Yes | Yes |
| 7 | IIb-4 | 25,100 | Yes | |
| 8 | IIb-1 | 25,000 | | |
| 9 | XIII-2 | 25,000 | | |
| 10 | IIb-5 | 23,300 | | |
| 11 | IV-3 | 22,000 | | |
| 12 | Icilin | 20,000 | | |
| 13 | V-4 | 17,500 | | |
| 14 | V-2 | 17,000 | | |
| 15 | V-1 | 9,600 | | |
| 16 | III-1 | 5,000 | | |
| 17 | DMSO control | 1,400 | | |

[1]Peak (FLIPR) is a measure of maximum calcium ion flux at 10 microM. FLIPR refers to Fluorometric Imaging Plate Reader; commercially available from, for example, Molecular Devices Corp.

V-1

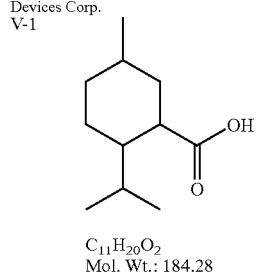

$C_{11}H_{20}O_2$
Mol. Wt.: 184.28

IIb-1

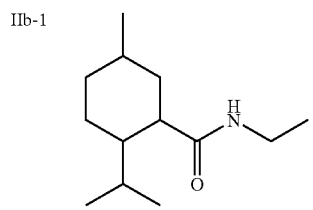

TABLE 1-continued

Ion Channel Activity and Cell Killing in Response to Selected CoolGenic Compounds.

| Activity Ranking | Compound ID# | Peak (FLIPR)[1] | 293/Trp-p8 Cell Killing | PC3/Trp-p8 Cell Killing |
|---|---|---|---|---|

$C_{13}H_{25}NO$
Mol. Wt.: 211.34

V-2

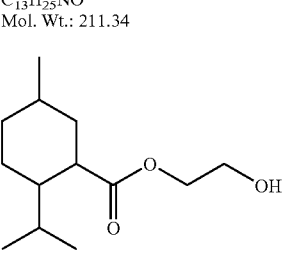

$C_{13}H_{24}O_3$
Mol. Wt.: 228.33

XIII-1

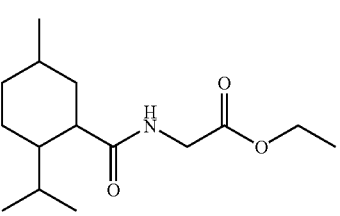

$C_{15}H_{27}NO_3$
Mol. Wt.: 269.38

IIb-2

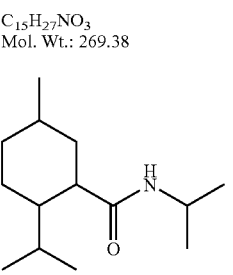

$C_{14}H_{27}NO$
Mol. Wt.: 225.37

IIb-3

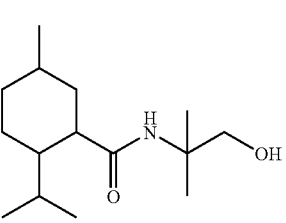

$C_{15}H_{29}NO_2$
Mol. Wt.: 255.40

IIa3-1

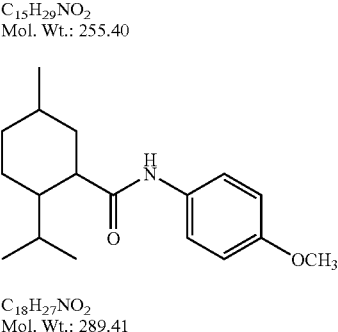

$C_{18}H_{27}NO_2$
Mol. Wt.: 289.41

TABLE 1-continued

Ion Channel Activity and Cell Killing in Response to Selected CoolGenic Compounds.

| Activity Ranking | Compound ID# | Peak (FLIPR)[1] | 293/Trp-p8 Cell Killing | PC3/Trp-p8 Cell Killing |
|---|---|---|---|---|

IIb-4

C$_{15}$H$_{29}$NO
Mol. Wt.: 239.40

III-1

C$_{10}$H$_{21}$NO
Mol. Wt.: 171.28

XIII-2

C$_{14}$H$_{25}$NO$_3$
Mol. Wt.: 255.35

IIb-5

C$_{15}$H$_{29}$NO
Mol. Wt.: 239.40

V-4

C$_{15}$H$_{28}$O$_4$
Mol. Wt.: 272.38

IV-1

C$_{15}$H$_{33}$OP
Mol. Wt.: 260.40

IV-2

C$_{13}$H$_{29}$OP
Mol. Wt.: 232.34

IV-3

C$_{14}$H$_{31}$OP
Mol. Wt.: 246.37

EXAMPLE 5

Preparation of Other Selected Compounds of Formula IIa. Example I was generally repeated for each of the following preparative compound examples with the exception that the amine (p-anisidine) co-reactant of Example I was substituted with the corresponding amine to produce compound having the structure indicated as the major product upon purification. The major product for each of the following examples was characterized by, for example, mass spectra to have a parent peak at about the molecular weight indicated.

IIa4-1

C$_{18}$H$_{27}$NO$_2$
Mol. Wt.: 289.41

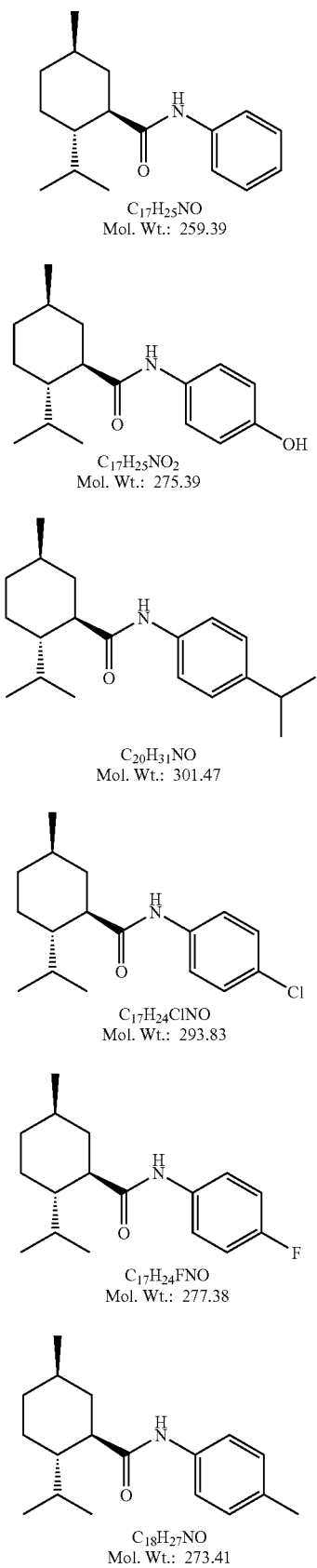

-continued

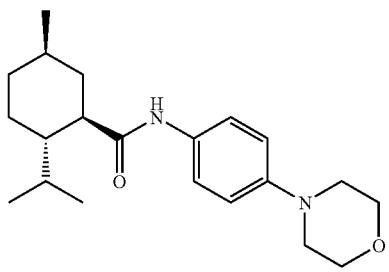

IIa4-9

$C_{21}H_{32}N_2O_2$
Mol. Wt.: 344.49

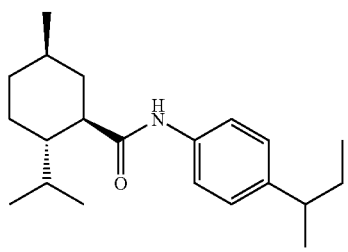

IIa4-10

$C_{21}H_{33}NO$
Mol. Wt.: 315.49

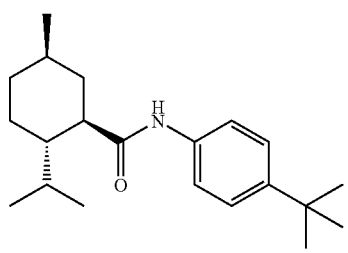

IIa4-11

$C_{21}H_{33}NO$
Mol. Wt.: 315.49

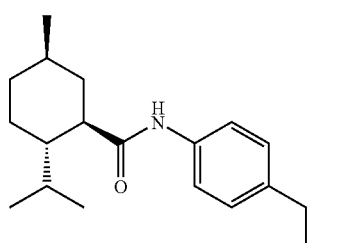

IIa4-12

$C_{20}H_{31}NO$
Mol. Wt.: 301.47

-continued

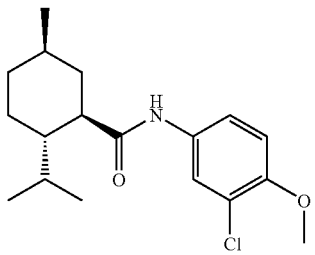

IIa6-2

$C_{18}H_{26}ClNO_2$
Mol. Wt.: 323.86

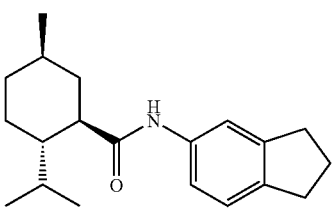

IIa6-3

$C_{20}H_{29}NO$
Mol. Wt.: 299.45

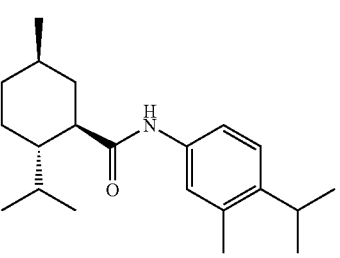

IIa6-4

$C_{21}H_{33}NO$
Mol. Wt.: 315.49

Table 2 summarizes $IC_{50}$ results for the indicated menthane carboxamide compounds on 293/Trp-p8.clone 18 and 293/Trp-p8.clone 10.

TABLE 2

$IC_{50}$ Data for Menthane Carboxamides on 293/Trp-p8.clone 18 and 293/Trp-p8.clone 10.

| Compound IIa2 where $R_1$ = H and $R_2$ = —$PhR_3R_4R_5R_6R_7$ is | Compound ID# | 293/Trp-p8.c18 | 293/Trp-p8.c10 |
|---|---|---|---|
| 4-MeO—Ph— | IIa4-1 | 0.58/0.45 | 0.42 |
| Ph— | IIa4-2 | 3.38 | 3.21 |
| 4-HO—Ph— | IIa4-3 | 1.05 | 1.23 |
| 3-MeO—Ph— | IIa10-1 | 3.69 | 3.80 |
| 4-iPr—Ph— | IIa4-4 | 0.98 | 0.76 |
| 2-MeO—Ph— | IIa8-1 | 17.57 | 16.74 |
| 4-Cl—Ph— | IIa4-5 | 17.57 | 1.99 |
| 4-F—Ph— | IIa4-6 | 3.78 | 3.58 |
| 3-F,4-MeO—Ph— | IIa6-1 | 0.60 | 0.79 |
| 4-Me—Ph— | IIa4-7 | 1.14 | 1.21 |
| 4-Et—Ph— | IIa4-8 | 0.68 | 0.73 |
| 2-Me, 4-MeO—Ph— | IIa12-1 | 0.93 | 1.14 |
| 3-F—Ph— | IIa10-2 | 2.91 | 6.31 |
| 4-morpholino-Ph— | IIa4-9 | 1.45 | 1.28 |
| 3-Cl, 4-Me—Ph— | IIa6-2 | 2.57 | 3.10 |
| 4-secBu—Ph— | IIa4-10 | 1.08 | 3.59 |
| 3,4-propyleneyl-Ph— (i.e., indanyl) | IIa6-3 | 1.71 | 1.35 |
| 4-tBuPh— | IIa4-11 | 1.41 | 1.23 |
| 4-nPrPh— | IIa4-12 | 4.93 | 5.65 |

TABLE 2-continued

IC$_{50}$ Data for Menthane Carboxamides
on 293/Trp-p8.clone 18 and 293/Trp-p8.clone 10.

| Compound IIa2 where $R_1$ = H and $R_2$ = —PhR$_3$R$_4$R$_5$R$_6$R$_7$ is | Compound ID# | 293/Trp-p8.c18 | 293/Trp-p8.c10 |
|---|---|---|---|
| 3-Me, 4-iPrPh— | IIa6-4 | 4.37 | 5.05 |
| Icilin (reference) | — | — | 79.24 |

EXAMPLE 6

Table 3 summarizes IC$_{50}$ duplicate results for the indicated menthane carboxamide compounds on 293/Trp-p8.clone 21.

TABLE 3

IC$_{50}$ Data for Menthane Carboxamides on PC3/Trp-p8.clone 21 (in duplicate).

| | Compound ID# | IC$_{50}$ |
|---|---|---|
| Compound IIa4 where R5— is | | |
| 4-MeO—Ph— | IIa4-1 | 1.642 |
| 4-HO—Ph— | IIa4-3 | 4.2696 |
| 4-iPr—Ph— | IIa4-4 | 3.2082 |
| 4-secBu—Ph— | IIa4-10 | 8.4937 |
| 4-nPr—Ph— | IIa4-12 | 12.857 |
| Compound IIa4 where R5 is | | |
| 4-MeO—Ph— | IIa4-1 | 1.5938 |
| 4-HO—Ph— | IIa4-3 | 3.7606 |
| 4-iPr—Ph— | IIa4-4 | 3.1039 |
| 4-secBu—Ph— | IIa4-10 | 48.613 |
| 4-nPr—Ph— | IIa4-12 | 16.473 |

EXAMPLE 7

Carrier articles, such as commercially available or custom manufactured implantable seeds or pellets, can be formulated and impregnated with one or more compound of the present disclosure, alone or in combination with another chemotherapeutic agent or other medicaments or excipients. A preferred formulation can have, for example, selectable timed-release characteristics for the coolgenic compound or other ingredients, for example, for use in prostate cancer treatment. For an example of non-radioactive sustained release implants in therapeutic cancer treatment, such as prostate cancer, see U.S. Pat. No. 5,633,274, which disclosure is incorporated herein by reference in its entirety.

EXAMPLE 8

The following illustrate representative pharmaceutical dosage forms, containing a compound of the disclosure ('Compound x'), such as a compound of formula I or II, for therapeutic or prophylactic use in humans.

| (i) Tablet 1 | mg/tablet |
|---|---|
| 'Compound x' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound x' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound x' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound x' | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound x' | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound x' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

EXAMPLE 9

Combination Therapy-Coadministration. The following illustrates representative pharmaceutical dosage forms, containing a compound of the disclosure in direct combination (admixture) with an antibody (collectively 'Composition y'), for therapeutic or prophylactic use in humans. Thus, for example, a compound of the disclosure, such as a compound of formula I or II, is combined with an antibody, such as an anti-VEGF antibody. The resulting combination, 'Composition y', is substituted in place of 'Compound x' in one or more of the above-mentioned injection formulations of EXAMPLE 8. The above formulations may be obtained by conventional procedures well known in the pharmaceutical arts.

EXAMPLE 10

Combination Therapy—Serial Administration. The following illustrates representative pharmaceutical dosage forms, containing a compound of the disclosure ('Compound x') in serial combination with an antibody ('antibody z'), for therapeutic or prophylactic use in humans. Thus, a compound of the disclosure, such as a compound of formula I or II, is serially administered with an antibody, such as an anti-VEGF antibody. For example, the serially administered combination can include first administration of a compound of the disclosure ('Compound x') is any of the above mentioned formulations of EXAMPLE 7 or 8 followed by a second injection administration of an antibody ('antibody z'). Alternatively, 'antibody z' is administered first followed by the administration of 'Compound x'. The above formulations may be obtained by conventional procedures well known in the pharmaceutical arts.

EXAMPLE 11

Methods, examples, and additional literature references for the preparation of antibodies, and characterization of antibodies, including antigen specificity, epitope mapping, isotyping, binding affinity, are disclosed in the aforementioned U.S. Pat. No. 6,582,959.

All publications, patents, and patent documents are incorporated by reference herein in their entirety, as though individually incorporated by reference. The disclosure has been described with reference to various specific and preferred embodiments and techniques. However, it should be understood that many variations and modifications can be made while remaining within the spirit and scope of the disclosure.

The claimed invention is:

1. A method of inducing apoptosis in prostate cancerous cells, the method comprising contacting the cancerous cells comprising prostate cancer cells expressing a Trp-p-8 receptor with an effective apoptosis-inducing amount of a compound of the formula (II)

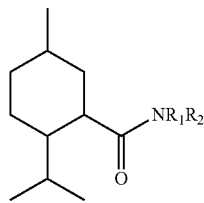

wherein $R_1$ and $R_2$ are each independently H, alkyl, or phenyl or substituted phenyl;
or a pharmaceutically acceptable salt thereof.

2. A method for killing or inhibiting the growth of prostate cancer cells expressing a Trp-p-8 receptor, comprising administering to said Trp-p-8 expressing prostate cancer cells an effective inhibitory amount of a compound of formula (II),

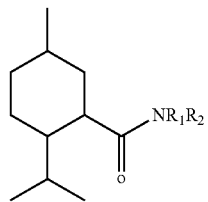

wherein $R_1$ and $R_2$ are each independently H, alkyl, or phenyl or substituted phenyl;
or a pharmaceutically acceptable salt thereof.

3. A method for stimulating Trp-p-8 receptor mediated calcium uptake in a cell comprising administering an effective amount of a compound of formula (II)

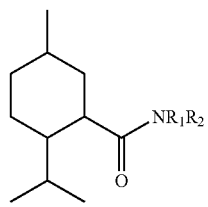

wherein $R_1$ and $R_2$ are each independently H, alkyl, or phenyl or substituted phenyl;
or a pharmaceutically acceptable salt thereof to the cell, wherein the cell expresses a Trp-p-8 receptor.

4. The method of claim 2 further comprising administering the compound of formula II in combination with an antibody, which antibody causes apoptosis, inhibits angiogenesis, or both.

5. The method of claim 4 wherein the antibody is a VEGF antibody.

6. The method of claim 2;
wherein
$R^1$ is H, or $(C_1-C_6)$alkyl;
$R^2$ is phenyl or a substituted phenyl of the formula $(-PhR_3R_4R_5R_6R_7)$

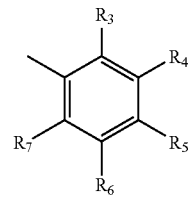

where
$R_3$, $R_4$, $R_6$, and $R_7$ are each independently —H, $(C_1-C_6)$alkyl, $(C_1-C_6)$alkoxyl, or halo;
$R_5$ is halo, $(C_1-C_6)$alkyl, $(C_3-C_{12})$cycloalkyl, $(C_1-C_6)$alkoxyl, —C(=O)$(C_1-C_6)$alkyl or $(C_1-C_7)$alkanoyl;
or $R_5$ is —$NR_8R_9$, where $R_8$ and $R_9$ are each independently —H, $(C_1-C_6)$alkyl, or $R_8$ and $R_9$ together with the nitrogen to which they are attached form a morpholino, pyrrolidino, piperidino, piperzino, indolino, benzimidazolino, azetidino, aziridino, azepino, 1,4-oxazino, or thiomorpholino ring;

or R$_4$ and R$_5$ together with the phenyl to which they are attached form a ring having 4 to 7 atoms and the ring having from 1 to 3 unsaturations; and stereoisomeric forms, mixtures of stereoisomeric forms; or a pharmaceutically acceptable salt thereof, provided that when R$_3$, R$_4$, R$_6$, and R$_7$ of -PhR$_3$R$_4$R$_5$R$_6$R$_7$ are —H, R$_5$ is other than —CH$_3$, —OCH$_3$, —OH, —F, or —NO$_2$; and provided that R$_2$ is other than 3-hydroxy-4-methyl-phenyl; and further provided that R$_2$ is other than 2-hydroxy-naphthyl, or pyridyl.

7. The method of claim 2, wherein R$_1$ and R$_2$ of formula II are each independently H or alkyl.

8. The method of claim 1, wherein the compound of the formula II is selected from the group consisting of:
2-Isopropyl-5-methyl-cyclohexanecarboxylic acid (4-methoxy-phenyl)-amide;
2-Isopropyl-5-methyl-cyclohexanecarboxylic acid (4-morpholin-4-yl-phenyl)-amide;
2-Isopropyl-5-methyl-cyclohexanecarboxylic acid (3-chloro-4-methoxy-phenyl)-amide;
2-Isopropyl-5-methyl-cyclohexanecarboxylic acid (4-sec-butyl-phenyl)-amide;
2-Isopropyl-5-methyl-cyclohexanecarboxylic acid (4-tert-butyl-phenyl)-amide;
2-Isopropyl-5-methyl-cyclohexanecarboxylic acid (4-propyl-phenyl)-amide;
2-Isopropyl-5-methyl-cyclohexanecarboxylic acid (4-isopropyl-3-methyl-phenyl)-amide;
a pharmaceutically acceptable salt thereof; and
a mixture thereof.

9. The method of claim 1, wherein the compound of the formula II is selected from the group consisting of:
N-ethyl-2-isopropyl-5-methylcyclohexanecarboxamide;
N,2-diisopropyl-5-methylcyclohexanecarboxamide;
N-(1-hydroxy-2-methylpropan-2-yl)-2-isopropyl-5-methylcyclohexanecarboxamide;
N-tert-butyl-2-isopropyl-5-methylcyclohexanecarboxamide;
N-sec-butyl-2-isopropyl-5-methylcyclohexanecarboxamide;
a pharmaceutically acceptable salt thereof; and
a mixture thereof.

10. The method of claim 2, wherein the compound of the formula II is selected from the group consisting of :
2-Isopropyl-5-methyl-cyclohexanecarboxylic acid (4-methoxy-phenyl)-amide;
2-Isopropyl-5-methyl-cyclohexanecarboxylic acid (4-morpholin-4-yl-phenyl)-amide;
2-Isopropyl-5-methyl-cyclohexanecarboxylic acid (3-chloro-4-methoxy-phenyl)-amide;
2-Isopropyl-5-methyl-cyclohexanecarboxylic acid (4-sec-butyl-phenyl)-amide;
2-Isopropyl-5-methyl-cyclohexanecarboxylic acid (4-tert-butyl-phenyl)-amide;
2-Isopropyl-5-methyl-cyclohexanecarboxylic acid (4-propyl-phenyl)-amide;
2-Isopropyl-5-methyl-cyclohexanecarboxylic acid (4-isopropyl-3-methyl-phenyl)-amide;
a pharmaceutically acceptable salt thereof; and
a mixture thereof.

11. The method of claim 2, wherein the compound of the formula II is selected from the group consisting of:
N-ethyl-2-isopropyl-5-methylcyclohexanecarboxamide;
N,2-diisopropyl-5-methylcyclohexanecarboxamide;
N-(1-hydroxy-2-methylpropan-2-yl)-2-isopropyl-5-methylcyclohexanecarboxamide;
N-tert-butyl-2-isopropyl-5-methylcyclohexanecarboxamide;
N-sec-butyl-2-isopropyl-5-methylcyclohexanecarboxamide;
a pharmaceutically acceptable salt thereof; and
a mixture thereof.

12. The method of claim 3, wherein the compound of the formula II is selected from the group consisting of :
2-Isopropyl-5-methyl-cyclohexanecarboxylic acid (4-methoxy-phenyl)-amide;
2-Isopropyl-5-methyl-cyclohexanecarboxylic acid (4-morpholin-4-yl-phenyl)-amide;
2-Isopropyl-5-methyl-cyclohexanecarboxylic acid (3-chloro-4-methoxy-phenyl)-amide;
2-Isopropyl-5-methyl-cyclohexanecarboxylic acid (4-sec-butyl-phenyl)-amide;
2-Isopropyl-5-methyl-cyclohexanecarboxylic acid (4-tert-butyl-phenyl)-amide;
2-Isopropyl-5-methyl-cyclohexanecarboxylic acid (4-propyl-phenyl)-amide;
2-Isopropyl-5-methyl-cyclohexanecarboxylic acid (4-isopropyl-3-methyl-phenyl)-amide;
a pharmaceutically acceptable salt thereof; and
a mixture thereof.

13. The method of claim 3, wherein the compound of the formula II is selected from the group consisting of:
N-ethyl-2-isopropyl-5-methylcyclohexanecarboxamide;
N,2-diisopropyl-5-methylcyclohexanecarboxamide;
N-(1-hydroxy-2-methylpropan-2-yl)-2-isopropyl-5-methylcyclohexanecarboxamide;
N-tert-butyl-2-isopropyl-5-methylcyclohexanecarboxamide;
N-sec-butyl-2-isopropyl-5-methylcyclohexanecarboxamide;
a pharmaceutically acceptable salt thereof; and
a mixture thereof.

* * * * *